(12) United States Patent
De Mooij

(10) Patent No.: US 12,280,272 B2
(45) Date of Patent: Apr. 22, 2025

(54) SYSTEM, METHOD AND KIT FOR IMMOBILIZATION OF A HUMAN'S BODY PART

(71) Applicant: MACROMEDICS B.V., Moordrecht (NL)

(72) Inventor: Leendert Gerrit De Mooij, Moordrecht (NL)

(73) Assignee: MACROMEDICS B.V., Moordrecht (NL)

(*) Notice: Subject to any disclaimer, the term of this patent is extended or adjusted under 35 U.S.C. 154(b) by 335 days.

(21) Appl. No.: 17/750,384

(22) Filed: May 22, 2022

(65) Prior Publication Data

US 2022/0370827 A1    Nov. 24, 2022

(30) Foreign Application Priority Data

May 21, 2021   (EP) ..................................... 21175473

(51) Int. Cl.
*A61N 5/10*         (2006.01)
*A61B 90/18*        (2016.01)

(52) U.S. Cl.
CPC ............. *A61N 5/10* (2013.01); *A61B 90/18* (2016.02); *A61N 2005/1097* (2013.01)

(58) Field of Classification Search
None
See application file for complete search history.

(56) References Cited

U.S. PATENT DOCUMENTS

| 10,470,957 B1* | 11/2019 | Denis ....................... A61G 7/07 |
| 2010/0000549 A1 | 1/2010 | Nieberding |
| 2019/0038377 A1* | 2/2019 | Wortmann ............. A61B 90/14 |

FOREIGN PATENT DOCUMENTS

| EP | 2846694 | 3/2015 |
| WO | 2016124232 A1 | 8/2016 |

* cited by examiner

*Primary Examiner* — Eliza W Osenbaugh-Stewart
(74) *Attorney, Agent, or Firm* — Hodgson Russ LLP

(57) ABSTRACT

A device for immobilization of a patient body part for radiotherapy applications includes at least one flanged support member and at least one support member fixation means for mounting the at least one flanged support member to a fixation surface at a distance from said fixation surface. The at least one flanged support member is adapted to receive and retain a first and optionally a second frame. The curved extension is adapted to retain the first frame or the first frame and the second frame. The invention also relates to a system, a method and a kit.

18 Claims, 25 Drawing Sheets

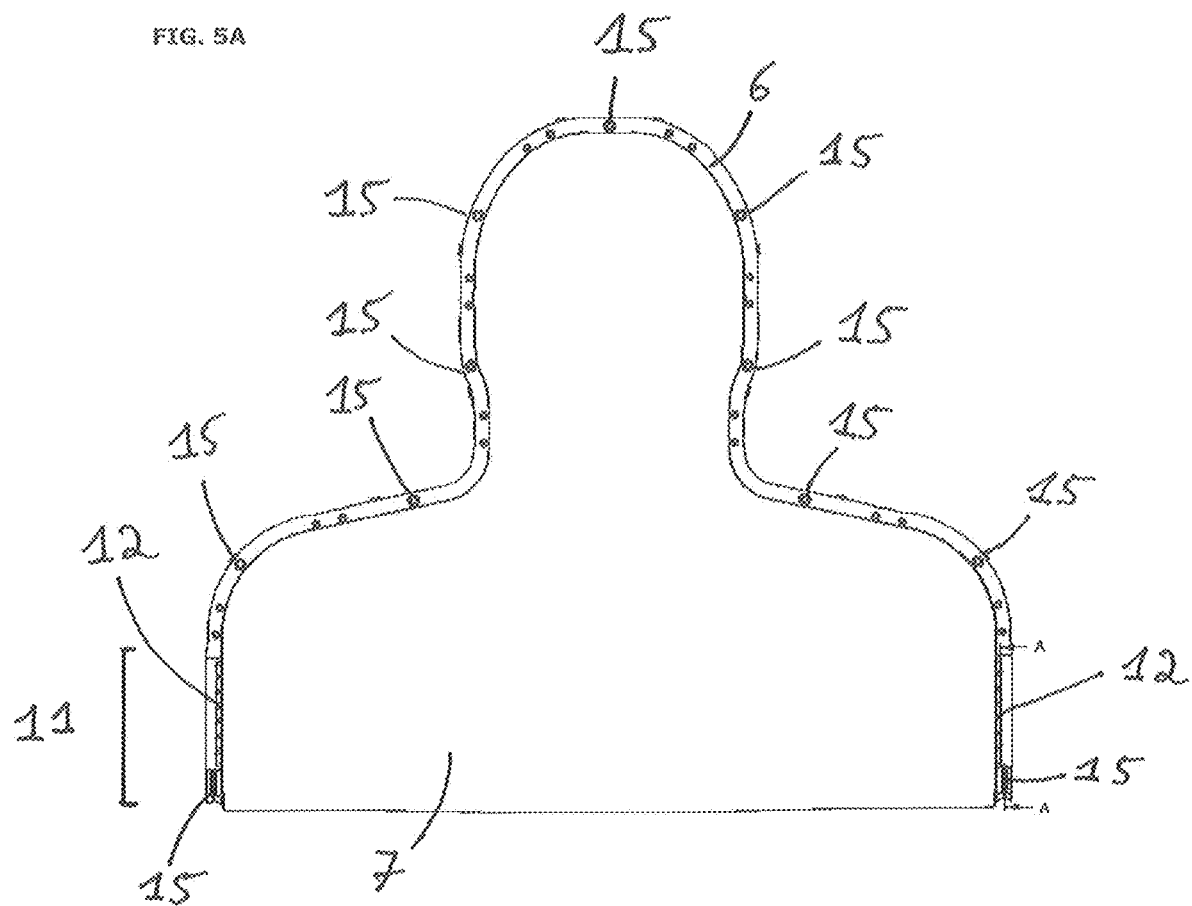
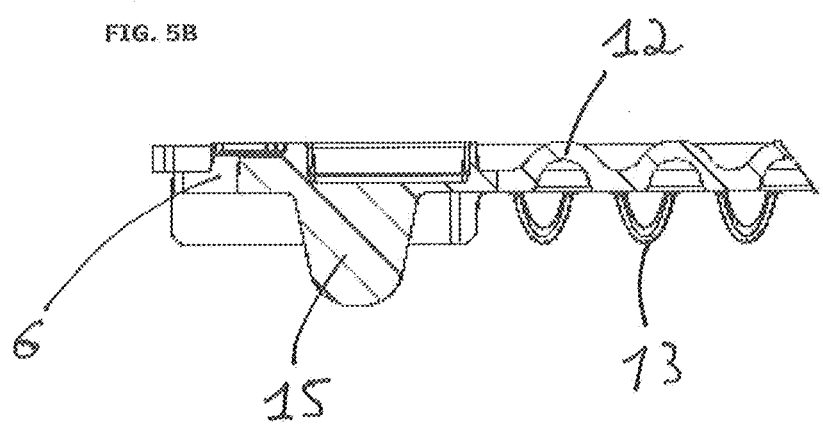

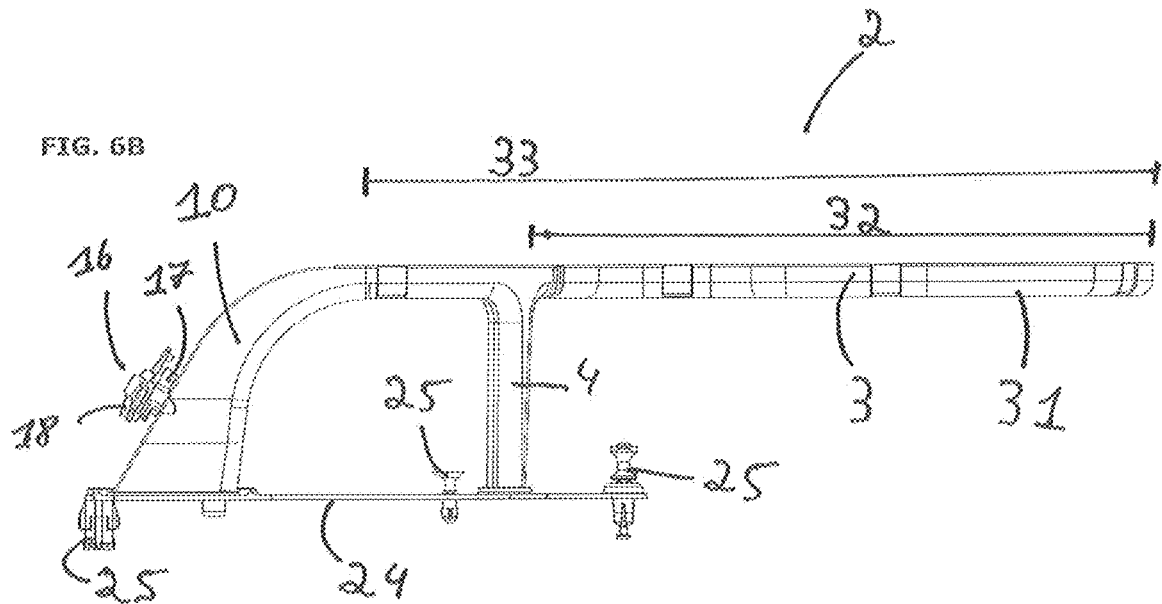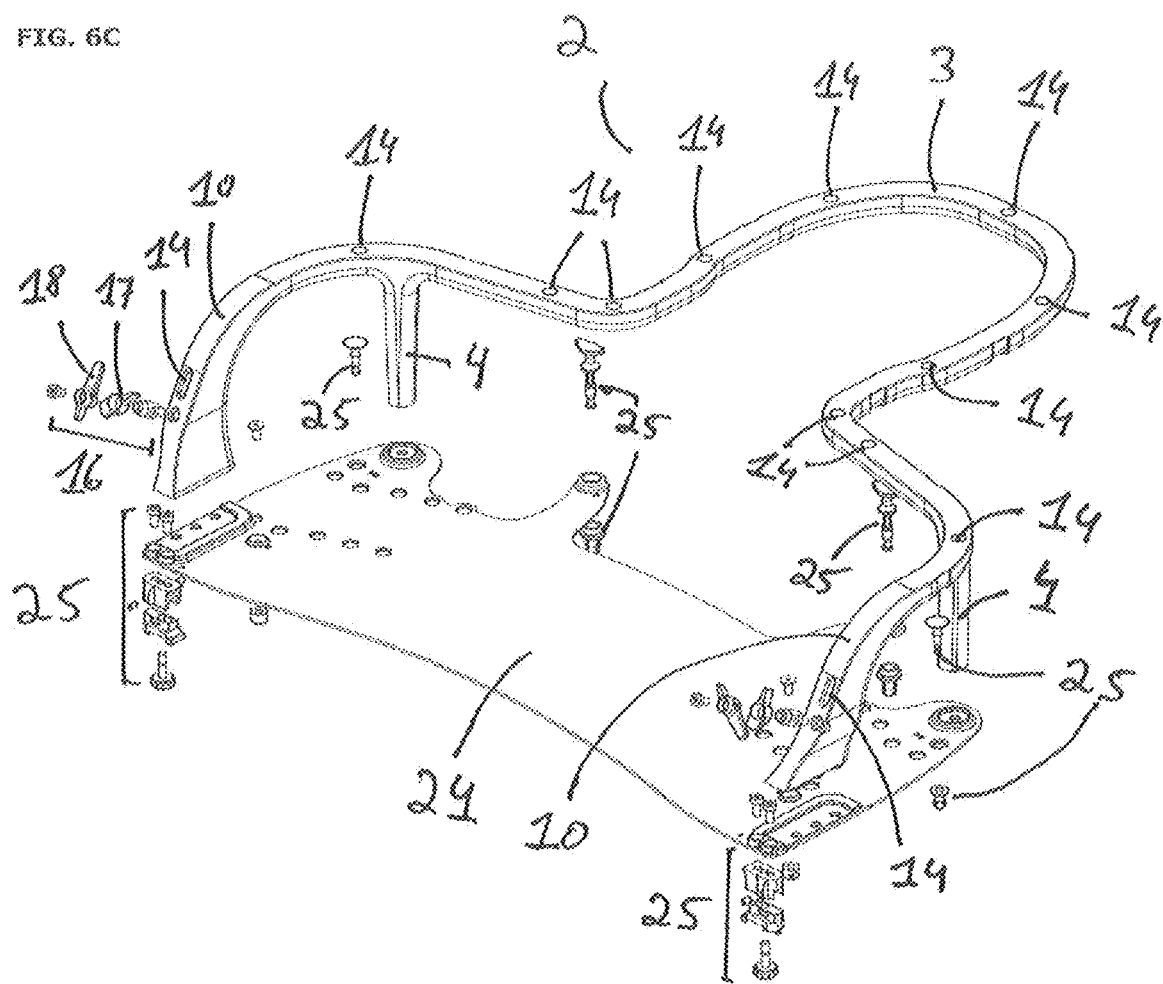

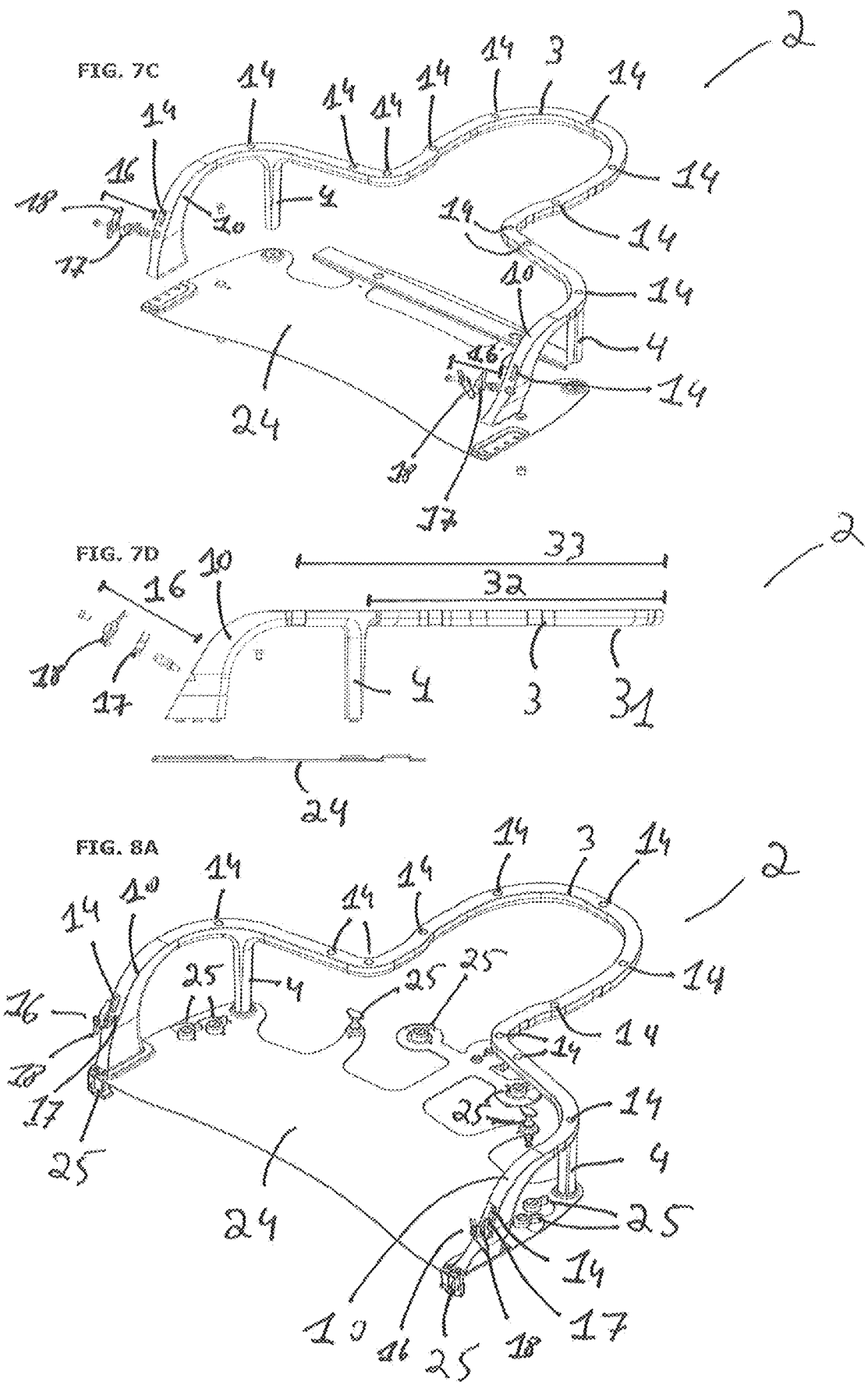

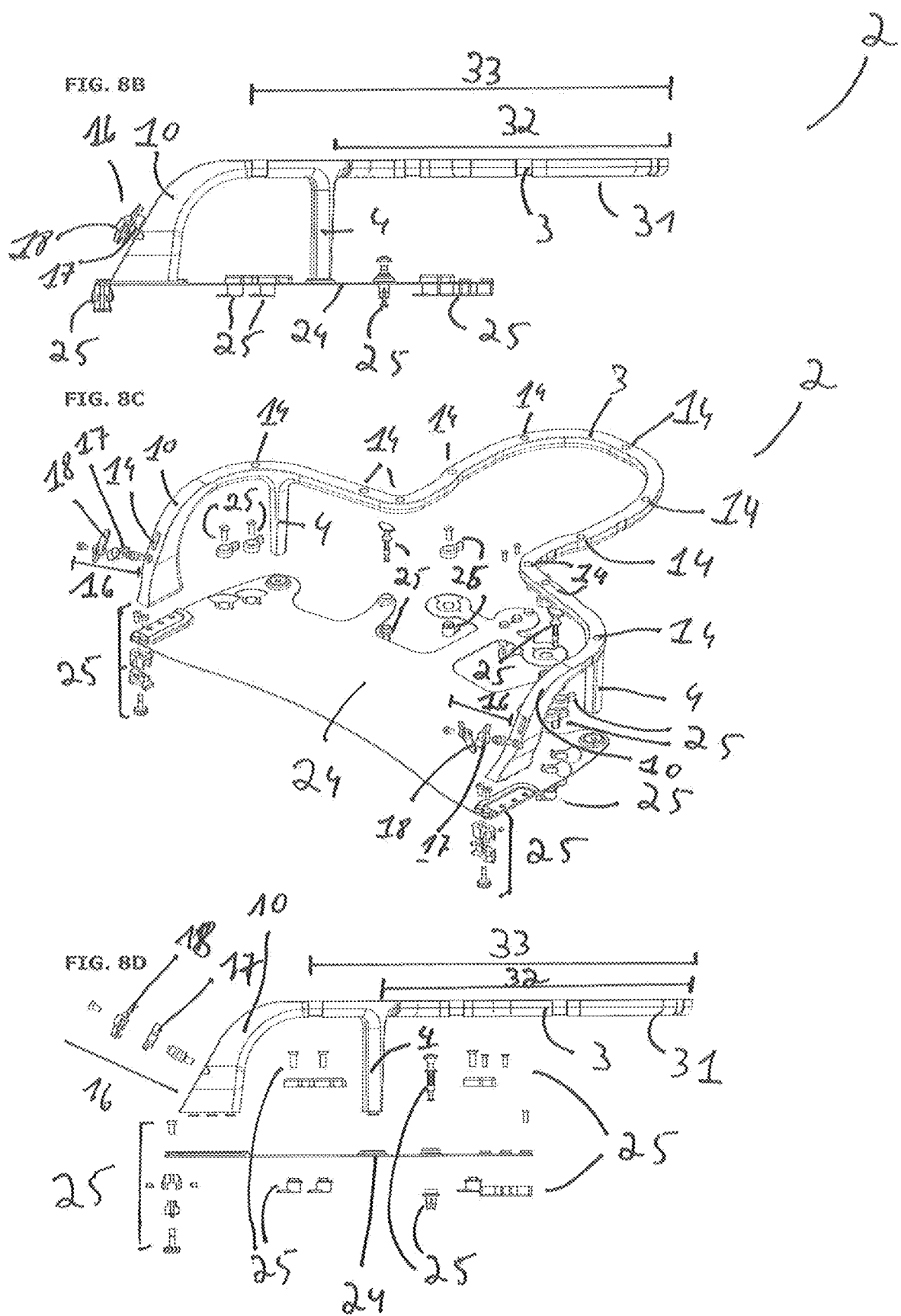

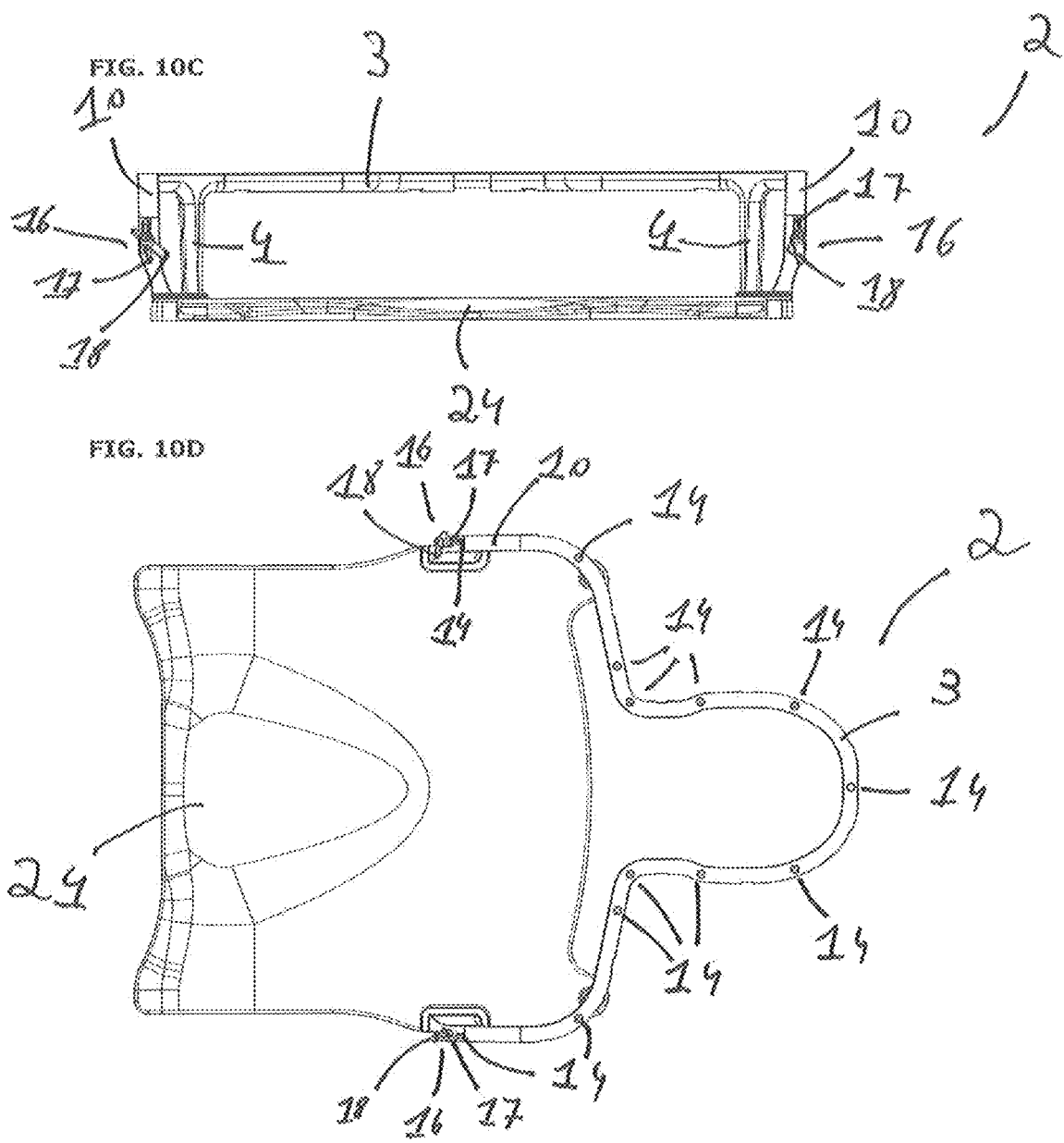

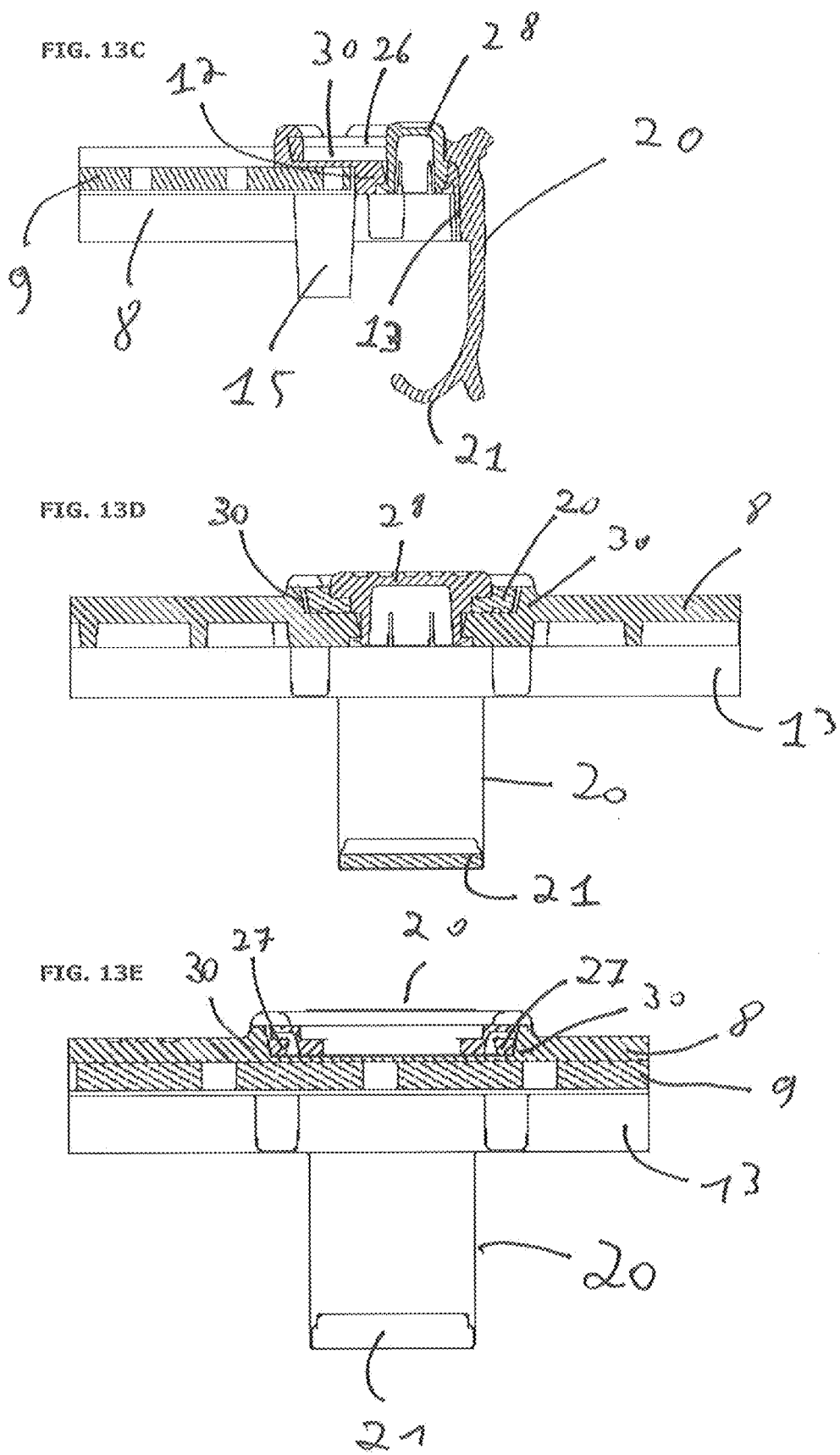

SYSTEM, METHOD AND KIT FOR IMMOBILIZATION OF A HUMAN'S BODY PART

CROSS-REFERENCE TO RELATED APPLICATIONS

This application claims priority to European Patent App. No. 21175473.4 filed May 21, 2021, the disclosure of which is hereby incorporated by reference.

FIELD OF THE INVENTION

The present invention pertains to a system, a method and a kit for immobilizing at least part of a human's body part for receiving radiation treatment. The invention is suitable for use in the medical field, particularly for immobilization purposes in radiotherapy and cancer treatment.

BACKGROUND

The treatment of patients having cancer frequently makes use of radiation therapy wherein radiation is directed to particular sites in the patient's body. These treatments require high precision, reliable and accurate patient set-up to position and immobilize the relevant portion of the patient's body undergoing the radiation. Various devices and equipment are available for effecting such action. For example, patient couches or tables are commonly provided at the radiation machine, e.g., linear accelerator, CT machine, MRI, etc., to support the patient in a prone or supine position while the relevant portion of the patient's body is held in a fixed or immobilized condition. To that end the immobilization of the relevant portion of the patient's body is commonly achieved by various types of devices mounted on the patient couch/treatment table.

A commonly used body part (i.e. the head) restraint device is a mask that is placed over the face of the patient to hold the patient's head stationary. Such masks may be molded to conform to the contours of the patient's face to ensure maximum immobilization. The back of the patient's head and contiguous portion of the patient's neck may be supported by a cushion which itself can be pre-contoured to a specific shape or can be conformed, e.g., molded, to the shape of the back of the patient's head. The mask itself can be pre-formed to a shape that will generally conform to the contours of the patient's face, or may be molded on the patient's face to closely conform to those contours. The molding of the mask is typically conducted preceding the first treatment. After this the mask can be mounted on the head of the patient and subsequently will be fixed to the patient support table. However, the patient's head and neck will still have to be supported, such as by cushions filled with granular material, for example, or by preformed cushions. Here, too, deviations in the position of the head in relation to the preceding treatment can easily occur.

EP 2 846 694 discloses a device, system and method for immobilization of a human's body part. The system comprises one flanged support member that is mounted to a fixation surface and two sheets received and retained by the flanged support member. The two sheets form a double shell mask enclosing the body part and supporting the body part free from the fixation surface. The disclosed system has the advantage that the body part enclosed in the double shell mask is well immobilized and that a practitioner has easy access to the enclosed body part.

A drawback of this known system is that it can only immobilize body parts that are completely free of the fixation surface, for instance a head, arms or legs. Body parts close to the trunk of the patient resting on the fixation surface cannot be immobilized with a double shell mask, but only with a single sheet above that body part that is directly attached to the fixation surface. This is for instance the case for the neck, shoulders, upper arms and upper legs. This results in suboptimal immobilization of these body parts, what has an adverse influence on radiotherapy for these body parts.

Another disadvantage of this system is that although for instance a head or arm can be comfortably immobilized, the neck, shoulders, upper arms and upper legs are not supported. This could cause fatigue or discomfort in these body parts, even when these body parts do not need to be immobilized for radiotherapy.

Still another disadvantage of this know immobilization system is that it comprises several nuts, bolts and screws that needs to be attached which, on one hand, represents a high workload for the practitioner and on the other hand, prolongs the time required for preparing the patient for radiotherapy thereby providing the patient with an uncomfortable feeling.

The aim of the present invention is to provide a solution to overcome at least part of the abovementioned disadvantages. The invention thereto aims to provide a system, a method and a kit which are highly effective and easy to use and apply for improved immobilization of a patient body part.

SUMMARY OF THE INVENTION

In a first aspect, the present invention relates to a system. Such a system is beneficial because it comprises at least one flanged support member, comprising at one side a curved extension towards the fixation surface, wherein the first frame or the first frame and the optional second frame are bent to follow the curved extension of the at least one flanged support member.

The advantage thereof is that also body parts close to the trunk of a patient resting on the fixation surface can be immobilized with a double shell mask. Because the first frame and second frame are bent towards the fixation surface, the double shell mask formed by the first sheet and second sheet can closely join body parts near the trunk of the patient. Because the at least one flanged support member comprises a curved extension, the first and the second frame, and consequently the first sheet and the second sheet, are also in this region firmly positioned. All this results in an optimal immobilization of said body parts, e.g. neck, shoulders, upper arms and upper legs, and a positive influence on the accuracy of radiotherapy for these body parts.

Another advantage of a system according to the current invention is that for instance neck, shoulders, upper arms and upper legs can be comfortably supported, even when immobilization of these body parts is not required for radiotherapy, e.g. when receiving radiotherapy for a tumor in the head, causing less fatigue or discomfort in these body parts. Important is that discomfort of the patient during treatment will force the patient to move the body to avoid pressure points and pain, causing movements and displacements in the treatment area. Modern, nowadays treatments in a MR-Linac as well as with AccuRay Cyberknife and other treatment methods are more and more exceeding a 30 to 45 minutes treatment time. When immobilization of these body parts is not required, the second frame and the second sheet can be limited to the body part that needs to be immobilized for radiotherapy, resulting in a double shell mask that is limited to for instance the head, while the head, neck and shoulders are completely supported by the first sheet. For some therapies it is even not required that the body part receiving radiotherapy is completely immobilized, but only supported. In that case the use of the first frame is sufficient.

Preferred embodiments of the device are disclosed herein.

A specific preferred embodiment relates to an embodiment of the device. In this embodiment the first frame or the first frame and the second frame comprise at least at one side a deformable part, wherein the deformable part is deformable in a direction transverse to the fixation surface. This is advantageous because the first frame and the second frame can be flat before initial use, thereby requiring less space for storage. This is additionally advantageous because the first frame and the second frame can be used with different types of flanged support members, which comprise curved extensions with different angles towards the fixation surface. By deforming the deformable part, the first frame and the second frame can be easily adapted to the corresponding angle of the curved extension. Important is that due to the bending of the first frame or the first frame and the second frame and the sheets in the receptive area where the patient will make contact with the moldable thermoplastic sheet, the strain transfer of forces applied once receiving the patient at the start of and during the molding and deforming process, the angle of the caudal part of the thermoplastic sheet will be in line with the angle of the patient's upper body.

In a second aspect, the present invention relates to a method. The method is advantageous because body parts close to the trunk of a patient resting on the fixation surface are immobilized with a double shell mask, resulting in an optimal immobilization of said body parts, e.g. neck, shoulders, upper arms and upper legs, and having a positive influence on the accuracy of radiotherapy for these body parts. Additionally, advantageous about the method is that these body parts near the trunk are comfortably supported, even when immobilization of these body parts is not required for radiotherapy, causing less fatigue or discomfort in these body parts and also avoiding pressure points. When immobilization of these body parts is not required, the second frame and sheet can be limited to the body part that needs to be immobilized for radiotherapy. For some therapies it is even not required that the body part receiving radiotherapy is immobilized, but only supported. In that case the use of the first frame is sufficient.

Preferred embodiments of the method are disclosed herein.

In a third aspect the present invention relates to a kit. The kit as described herein provides an advantageous effect that with a limited number of elements and without a high workload for the practitioner a body part of a patient can be comfortably and optimally immobilized with a double shell mask, even when the body part is close to the trunk of the patient. In case the body part receiving radiotherapy only needs to be supported, only the first frame is required.

Preferred embodiments of the kit are disclosed herein.

In a fourth aspect, the present invention relates to a device. Such a device is beneficial because it comprises at least one flanged support member, comprising at one side a curved extension towards the fixation surface, the curved extension adapted to retain a first frame or a first frame and a second frame. The advantage thereof is that also body parts close to the trunk of a patient resting on the fixation surface can be immobilized with a double shell mask, because a first frame and a second frame that are bent towards the fixation surface, can be attached to the curved extension, firmly positioning the first frame and the second frame next to body parts near the trunk of the patient. This results in an optimal immobilization of said body parts and a positive influence on the accuracy of radiotherapy for these body parts. In case the body part receiving radiotherapy only needs to be supported, only the first frame is required. Body parts near the trunk are comfortably supported, causing less fatigue or discomfort in these body parts and also avoiding pressure points.

DESCRIPTION OF FIGURES

FIG. 5A shows a top view of a first frame for head and shoulder immobilization according to an embodiment of the current invention.

FIG. 5B shows a cross section of the first frame of FIG. 5A along the line AA.

FIG. 6B shows a side view of the device of FIG. 6A.

FIG. 6C shows an exploded three-dimensional representation of the device of FIG. 6A.

FIG. 7C shows an exploded three-dimensional representation of the device of FIG. 7A.

FIG. 7D shows an exploded side view of the device of FIG. 7A.

FIG. 8A shows a three-dimensional representation of another alternative device according to an embodiment of the current invention.

FIG. 8B shows a side view of the device of FIG. 8A.

FIG. 8C shows an exploded three-dimensional representation of the device of FIG. 8A.

FIG. 8D shows an exploded side view of the device of FIG. 8A.

FIG. 10C shows a front view of the device of FIG. 10A.

FIG. 10D shows a top view of the device of FIG. 10A.

FIG. 13C shows a cross section of a clamp of FIG. 13A according to an embodiment of the current invention in a direction transverse to the clamp.

FIG. 13D shows a cross section of a clamp of FIG. 13A at a first location in a direction parallel with the clamp.

FIG. 13E shows a cross section of a clamp of FIG. 13A at a second location in a direction parallel with the clamp.

DETAILED DESCRIPTION OF THE INVENTION

Figure 1A:
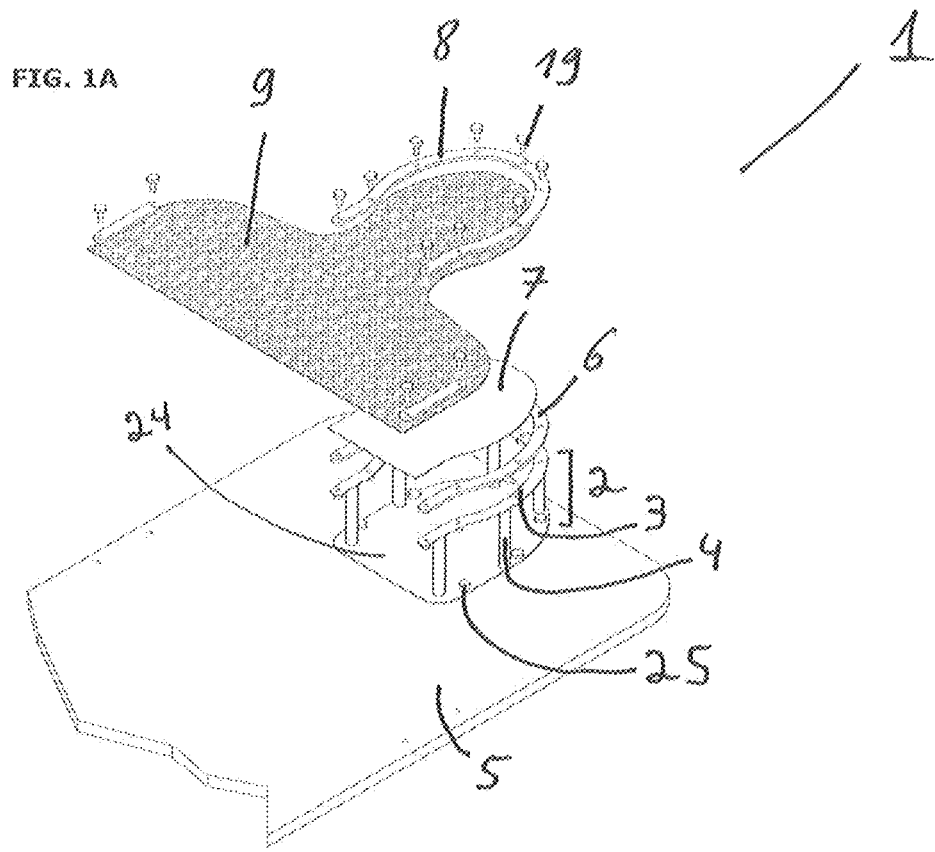
FIG. 1A shows an exploded-view of a system according to the prior art.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

As used herein, the following terms have the following meanings:

"A", "an", and "the" as used herein refers to both singular and plural referents unless the context clearly dictates otherwise. By way of example, "a compartment" refers to one or more than one compartment.

"Comprise", "comprising", and "comprises" and "comprised of" as used herein are synonymous with "include", "including", "includes" or "contain", "containing", "contains" and are inclusive or open-ended terms that specifies the presence of what follows e.g. component and do not exclude or preclude the presence of additional, non-recited components, features, element, members, steps, known in the art or disclosed therein.

Furthermore, the terms first, second, third and the like in the description and in the claims, are used for distinguishing between similar elements and not necessarily for describing a sequential or chronological order, unless specified. It is to be understood that the terms so used are interchangeable under appropriate circumstances and that the embodiments of the invention described herein are capable of operation in other sequences than described or illustrated herein.

The recitation of numerical ranges by endpoints includes all numbers and fractions subsumed within that range, as well as the recited endpoints.

Whereas the terms "one or more" or "at least one", such as one or more or at least one member(s) of a group of members, is clear per se, by means of further exemplification, the term encompasses inter alia a reference to any one of said members, or to any two or more of said members, such as, e.g., any ≥3, ≥4, ≥5, ≥6 or ≥7 etc. of said members, and up to all said members.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

The term "initial state" of a thermoplastic sheet used herein refers to a thermoplastic sheet which is still flat and not yet deformed. The term "final state" of a thermoplastic sheet used herein refers to a thermoplastic sheet which has been deformed to conform the anatomical contours of a body portion and cured thereby having a rigid molded thermoplastic sheet.

The term "cured" used herein refers to a thermoplastic sheet that was heated, deformed according to a patient's body part anatomical contours and cooled to ambient temperature such as to rigidify.

The terms "support fixation surface" and "fixation surface" are used herein as synonyms and refer to a surface to which the device according to the present invention is suitable to be mounted and/or fixed. Said fixation surface might be a radiation table for instance.

In a first aspect, the invention relates to a system for immobilization of a patient body part for radiotherapy applications.

In a preferred embodiment, the system comprises a device, a first frame and optionally a second frame.

The device comprises at least one flanged support member and at least one support member fixation means for mounting the at least one flanged support member to a fixation surface at a distance from said fixation surface. Preferably the at least one support member fixation means is mounting the at least one flanged support member substantially parallel to the fixation surface. The at least one flanged support member is adapted to receive and retain the first frame and the second frame. The at least one flanged support member is adapted for supporting the first frame and the second frame at a distance from the fixation surface. Preferably the at least one flanged support member comprises a flange with a similar shape as the first frame and the second frame. The at least one flanged support member comprises preferably attachment means for attaching the first frame and the second frame to the at least one flanged support member. Non-limitative examples are openings for receiving rivets, screws or bolts and snap fit means connections. The at least one flanged support member is provided with 5 to 20, preferably 7 to 15, more preferably 9 to 12 attachment means.

The first frame comprises a first sheet for covering anatomical contours of a first area of said body part. The first frame forms a circumferential rim for the first sheet. The first frame is placed on the flange of the at least one flanged support member and so supported by the at least one flanged support member.

The second frame comprises a second sheet for covering anatomical contours of a second area of said body part which is not covered by the first sheet. The second frame forms a circumferential rim for the second sheet. The second frame is superimposable on the first frame. Consequently, the second frame is supported by the at least one flanged support member.

A suitable material for the first and the second frame is for instance acrylonitrile-butadiene-styrene (ABS).

The first sheet and the second sheet are moldable thermoplastic sheets or preformed sheets or any other sheets suitable to be used in the context of the present invention and known to the person skilled in the art. The first sheet and the second sheet form a double shell mask enclosing said body part. The double shell mask ensures that the body part is well immobilized.

The at least one flanged support member comprises at one side a curved extension towards the fixation surface. Preferably the curved extension touches the fixation surface. This is advantageous as the curved extension serves also as a support member fixation means. The first frame or the first frame and the second frame are bent to follow the curved extension of the at least one flanged support member.

This embodiment is advantageous because also body parts close to the trunk of a patient resting on the fixation surface can be immobilized with a double shell mask. Because the first frame and second frame are bent towards the fixation surface, the double shell mask formed by the first sheet and second sheet can closely join body parts near the trunk of the patient. Because the at least one flanged support member comprises a curved extension, the first and the second frame, and consequently the first sheet and the second sheet, are also in this region firmly positioned. When the curved extension touches the fixation surface, the first sheet and second sheet can be firmly positioned up to a point in the immediate neighborhood of the patient's trunk. All this results in an optimal immobilization of said body parts, e.g. neck, shoulders, upper arms and upper legs, and a positive influence on the accuracy of radiotherapy for these body parts.

Another advantage is that for instance neck, shoulders, upper arms and upper legs can be comfortably supported, even when immobilization of these body parts is not required for radiotherapy, e.g. when receiving radiotherapy for a tumor in the head, causing less fatigue or discomfort in these body parts. When immobilization of these body parts is not required, the second frame and the second sheet can be limited to the body part that needs to be immobilized for radiotherapy, resulting in a double shell mask that is limited to for instance to the head, while the head, neck and shoulders are completely supported by the first sheet. In that case the second frame does not require a deformable part and preferably stops where the curved extension of the at least one support flanged member starts.

For some therapies it is even not required that the body part receiving radiotherapy is completely immobilized, but only supported. In that case the use of the first frame is sufficient.

In an embodiment the curved extension covers at least a 40 degree angle of a circle segment, preferably at least a 50 degree angle and more preferably at least a 55 degree angle. This guarantees that the curved extension is sufficiently bent towards the fixation surface and allows for sufficient separation between the supported body part and the fixation surface.

Preferably the curved extension covers at most a 70 degree angle of a circle segment, more preferably at most a 65 degree angle. Higher angles are uncomfortable for the patient.

In an embodiment the second sheet forms a chin strap and a head strap and the first sheet forms a support for shoulders, neck and head. The second sheet does not cover the remainder of the head, like nose, mouth and eyes. This is possible because the first sheet supports efficiently the shoulders, neck and head and is perfectly matching the anatomical contours of the shoulders, neck and head. For a number of applications this results already in a sufficient immobilization of the head. This embodiment is advantageous because it is not necessary to cover the face, giving more comfort to the patient.

In a preferred embodiment, the support member fixation means are selected from the group comprising upstanding circumferential support legs, upstanding walls provided with openings, upstanding pyramids, inverted pyramids or any other support member fixation means known to the person skilled in the art. Said support member fixation means can be of any shape. The height of said support member fixation means should be selected such as a free space is created between the fixation surface and the first sheet and second sheet when the body part is immobilized.

In a preferred embodiment, the thermoplastic first and second sheet have different elasticity. Preferably, before heating and/or molding, the elastic modulus ratio of the first sheet to the second sheet is from 2 to 8, preferably from 3 to 7, more preferably from 4 to 6, most preferably about 5.

Preferably, the elastic modulus of the first sheet before heating and/or molding is from 1200 to 2200 MPa, preferably from 1300 to 2000 MPa, more preferably from 1400 to 1800 MPa, even more preferably from 1500 to 1700 MPa or any value comprised in the mentioned ranges. Preferably, the elastic modulus of the first sheet is about 1600 MPa.

Preferably, the elastic modulus of the second sheet before heating and/or molding is from 100 to 600 MPa, preferably from 150 to 500 MPa, more preferably from 200 to 400 MPa, even more preferably from 250 to 350 MPa or any value comprised in the mentioned ranges. Preferably, the elastic modulus of the upper sheet is about 330 MPa.

This embodiment is advantageous because the body part can be supported free from the fixation surface without use of cushions or other support blocks.

In a preferred embodiment, the at least one flanged support member comprises a cantilevered part at a side opposite to the curved extension. The cantilevered part is free of support member fixation means. A cantilevered part is advantageous for having free access to the immobilized body part. A practitioner will have access and will be able to touch, support and shape the thermoplastic first sheet when the patient's body part, e.g. the head, is placed on the thermoplastic first sheet. The practitioner can than make sure that the thermoplastic first sheet is perfectly matching the anatomical contours of the body part. This is additionally advantageous for applying radiotherapy on a body part in a very limited and enclosed space, for instance a coil. The cantilevered part with the immobilized body part can be entered in the coil, not hindered by other structures like for instance support member fixation means. This embodiment is particular advantageous in combination with a previously described embodiment wherein the first sheet is less elastic than the second sheet.

In a further embodiment, the cantilevered part of the at least one flanged support member is at least 50% of a total length of the at least one flanged support member. The total length is measured from a point of the at least one flanged support member where the curved extension starts to a most extreme point at a side opposite to the curved extension, seen from the side of the device. The cantilevered part starts at a support member fixation means closest to said most extreme point. The cantilevered part of the at least one flanged support member is preferably at least 60% of a total length of the at least one flanged support member, more preferably at least 70% and even more preferably at least 75%.

In a preferred embodiment, the device comprises a base plate. Preferably said base plate is permanently or dismountably connected to said flanged support member by the support member fixation means. Preferably the curved extension of the at least one flanged support member touches the base plate. This is advantageous as the curved extension also serves as a support member fixation means. When the curved extension of the at least one flanged support member touches the base plate, it practically corresponds to touching the fixation surface. The base plate is provided with fixation means for mounting said base plate to a fixation surface. The base plate forms a plane. The plane of the base plate and the flange of the at least one flanged support member are substantially parallel to each other or form two angled planes to preposition the patient's body part depending on the treatment. The device might comprise a base plate which is connected to said at least one flanged support member by an open structure which preferably comprises a plurality of upstanding circumferential support legs.

In a preferred embodiment, the open structure, preferably comprising a plurality of upstanding circumferential support legs, or the support member fixation means separate the plane of the base plate or the plane of the fixation surface from the flange of the flanged support member by a distance d comprised between 5 and 100 cm, preferably between 10 and 90 cm, more preferably between 15 and 80 cm, even more preferably between 20 and 70 cm, most preferably between 25 and 60 cm, even most preferably between 30 and 50 cm.

In a preferred embodiment, the support legs are fiber tubes with a wall thickness of 0.2-2.0 mm and a weight between 150 and 250 gr/m2. Suitable materials for the support legs are Uni Directional carbon fibers, glass fibers or a combination of Uni Directional carbon fabrics and Cross Weave carbon fabrics. For optimal dosimetric properties, the wall thickness is between 0.2 and 0.5 mm. The support legs might be glued to the flanged support member and/or to the base plate. In the gluing areas the tubes are filled with low density foam, e.g. Rohacell 51 or 71, with a maximum length of 10-15 mm.

In a preferred embodiment, the device of the present invention has a shape which is open at one end. This is beneficial for receiving said body part while the trunk of the patient is located near the open end. The device is not a barrier for said body part. The at least one flanged support member has consequently also a shape which is open at one end. As described in a previous embodiment, the at least one flanged support member comprises preferably a flange with a similar shape as the first frame and the second frame. Consequently, the first frame and second frame have preferably also a shape which is open at one end. The curved extension of the at least one flanged support member is preferably located at the open end, because the trunk of the patient is near the open end.

For instance, the at least one flanged support member, the first frame and the second frame have a U-shape, adapted for immobilizing a human head. In another example the at least one flanged support member, the first frame or the first frame and the second frame have a shape corresponding to the contour of the head and shoulders of a patient. In yet another example the at least one flanged support member, the first frame or the first frame and the second frame have a shape corresponding to the contour of the upper arm, elbow, lower arm and hand of a patient.

In a preferred embodiment, the base plate is provided with fixation means for mounting the base plate, and hence mounting the device, to a support fixation surface such as table for radiation therapy. The support fixation surface is also provided with support surface fixation means which correspond to the base plate fixation means. The fixation means of the base plate and the corresponding fixation means of the support fixation surface are selected from the group comprising: rivets, screws, bolts and nuts, and snap fit means connections and foam or plastic pads or parts that will fit in recesses in the support fixation surface. Wherein the at least one flanged support member is mounted on the fixation surface using support member fixation means, the fixation surface is adapted to receive and fix said fixation means.

In a preferred embodiment, the device is manufactured from a material having a low density. More preferably, the device is manufactured from a carbon composite material, even more preferably from a carbon composite polymer, most preferably from carbon fiber reinforced plastics. This is advantageous as the device will have a low specific weight while having the necessary strength for holding the patient's body part during the production of the double shell mask. Alternatively the device is manufactured from glass fibers or aramid fibers. These fibers are well suited for use in a MRI environment. In a preferred embodiment, the weight of the device is comprised between 50 and 1000 g, preferably between 100 and 900 g, more preferably between 150 and 800 g.

In a preferred embodiment, the first and/or the second sheet might be provided with one or more openings. For instance an opening can be provided in the sheet covering a face of a patient. Said opening will be positioned such as to be at the level of the nose and/or the mouth such as to permit the patient to breathe.

In a preferred embodiment, the first frame or the first frame and the second frame comprise at least at one side a deformable part. The deformable part is deformable in a direction transverse to the fixation surface. This means that the deformable part is deformable in a direction transverse to a plane formed by the first frame and the first sheet, respectively the second frame and the second sheet. The deformable part is positioned at the side of the first frame and the second frame bent towards the fixation surface.

This embodiment is advantageous because the first frame and the second frame can be flat before initial use, thereby requiring less space for storage. This is additionally advantageous because the first frame and the second frame can be used with different types of flanged support members, which comprise curved extensions with different angles towards the fixation surface. By deforming the deformable part, the first frame and the second frame can be easily adapted to the corresponding angle of the curved extension.

In a further embodiment the deformable part of the first frame and the second frame is thermoplastic. This is especially beneficial in combination with a first thermoplastic sheet and a second thermoplastic sheet, because the first frame and the second frame can be deformed while the first sheet and the second sheet are already installed in respectively the first frame and the second frame, by heating the first frame and the second frame. An example of a suitable material is acrylonitrile-butadiene-styrene (ABS). This material is getting softer when heated, simplifying deformation.

In an alternative embodiment the deformable part of the first frame and the second frame is out of a flexible material. The flexible material allows deformation of the first frame and the second frame. The flexible material remains in a bent form after curing of the thermoplastic first sheet or the thermoplastic second sheet or after attaching a preformed first sheet or preformed second sheet.

In another alternative embodiment the deformable part of the first frame and the second frame is thinner compared to the remainder of the first frame, respectively the second frame. This is advantageous for allowing easy deformation of the first frame and the second frame. This embodiment can be advantageously combined with previously described embodiments wherein the deformable part is thermoplastic or wherein the deformable part is out of a flexible material.

The deformable part is preferably at least 1 mm thinner compared to the remainder of the first frame, respectively the second frame, more preferably at least 2 mm, even more preferably at least 3 mm.

The deformable part has preferably a thickness of at least 1 mm, more preferably at least 2 mm.

The deformable part has preferably a thickness of at most 4 mm, more preferably at most 3 mm.

In a preferred embodiment, the first frame and the second frame comprise at an inner side, directed towards said sheets, positioning means for positioning said sheets in said frames. The positioning means can be for instance protrusions or a ridge. The sheets can be correctly positioned in the first frame or second frame by placing the sheets on a surface of the first frame or second frame, adjacent to the positioning means. The sheets are glued or welded to the first frame or second frame. Thanks to the positioning means, the sheets are always correctly placed in the first frame and second frame for optimal support in a direction transverse to a plane formed by the frame and the sheet.

On the deformable part of said frames the positioning means are open and separated protrusions. Open protrusions are beneficial because less material is required for making the protrusions, resulting in light frames. Open and separated protrusions are additionally advantageous because it facilitates deforming the first frame and second frame in a direction transverse to the plane formed by the first frame and the first sheet, respectively the second frame and the second sheet. This contrasts with for instance a ridge as a positioning means.

The positioning means of the first frame are directed towards the second frame. This is advantageous to support the first sheet when said body part is supporting on the first sheet, because the surface of the first frame on which the first sheet is placed is between the fixation surface and the first sheet.

The positioning means of the second frame are directed towards the first frame. This is especially advantageous in combination with a thermoplastic second sheet during deformation of the second thermoplastic sheet for covering the anatomical contours of the second area of said body part, because the second sheet is between said body part and the surface of the second frame on which the second sheet is placed, avoid that the second sheet is pulled loose from the second frame during deformation.

In a preferred embodiment, the first frame and the second frame comprise guiding means for guiding the second frame to a correct position on the first frame and for guiding the first frame to a correct position on the at least one flanged support member. This is advantageous for an initial correct positioning of the first frame and the second frame before being attached to the at least one flanged support member, preferably using the previously described attachment means.

Preferably the guiding means of the first frame is a raised edge or protrusions at circumference of the first sheet of the first frame and a raised edge or protrusions at an outer circumference of the second frame. This is beneficial because when the first frame and the second frame are superimposed, the guiding means of the first frame and the second frame do not interfere.

On the deformable part of said frames the guiding means are separated protrusions. Separated protrusions are advantageous because it facilitates deforming the first frame and second frame in a direction transverse to the plane formed by the first frame and the first sheet, respectively the second frame and the second sheet. This is in contrast to for instance a raised edge as a positioning means.

In a preferred embodiment the deformable part of said frames has a corrugated surface. A corrugated surface is beneficial for deforming the first frame and second frame in a direction transverse to the plane formed by the first frame and the first sheet, respectively the second frame and the second sheet.

In a preferred embodiment, the at least one flanged support member comprises openings and the first frame and the second frame comprise corresponding protrusions, wherein the protrusions of the first frame are hollow and received in the openings of the at least one flanged support member and the curved extension and wherein the protrusions of the second frame are received in the hollow protrusions of the first frame.

This embodiment is beneficial to avoid that the first frame and the second frame can rotate or shift in the plane of the surface of the at least one flanged support member. This is especially beneficial in combination with thermoplastic sheets because during deformation of the first sheet, the first frame is not necessary already attached to the at least one flanged support member and the second sheet has to be deformed at least partly before it can be attached to the at least one flanged support member. The openings and the corresponding protrusions help to maintain relative positions of the first frame, the second frame and the at least one flanged support member during deformation of the thermoplastic sheets before the first and second frame are firmly attached to the at least one flanged support member. This embodiment is additionally advantageous to guarantee that the first frame and the second frame are correctly and consistently positioned to each other and to the at least one flanged support member when the first frame and the second frame are used for multiple radiotherapy sessions. This advantage is valid for thermoplastic as well as preformed sheets.

In a further embodiment the curved extensions comprises at least two openings and the first frame at least two complementary protrusions. The protrusions of the first frame received in the opening comprised in the curved extension can be hollow or massive. If the protrusions of the first frame are hollow, the second frame can comprise complementary protrusions, received in the protrusions of the first frame. This embodiment is advantageous for avoiding shift or rotation during deformation of the first sheet and where applicable the second sheet.

In a preferred embodiment, the device comprises a double lock mechanism. The double lock mechanism comprises a first rotatable lever and a second rotatable lever. The first rotatable lever and the second rotatable lever are stacked on each other. The first frame is locked to the first frame with the first rotatable lever in a first position and unlocked to the device with the first rotatable lever in a second position. The second frame is locked to the device with the second rotatable lever in a second position and unlocked to the device with the second rotatable lever in a second position. The first frame comprises preferably a corresponding notch for receiving the first rotatable lever. The second frame comprises preferably a corresponding notch for receiving the second rotatable lever. The double lock mechanism is preferably placed on the curved extension of the at least one flanged support member, more preferably a flat part of the curved extension, or on a support fixation means near the curved extension.

This embodiment is especially advantageous for attaching the first frame and the second frame on the curved extension of the at least one flanged support member in combination with thermoplastic sheets and with first frames or first frames and second frames comprising a deformable part. When deforming the thermoplastic first sheet or the thermoplastic second sheet to anatomical contours of said body part, pressure is applied to the first sheet or the second sheet, consequently also resulting in forces on the first frame, respectively the second frame. These forces could cause deformation of the deformable part of the first frame, respectively the second frame in a direction away from the fixation surface. The double lock mechanism allows for already attaching the first frame and subsequently the second frame to the at least one flanged support member before both the first frame and the second frame are installed and attached on the at least one flanged support member. A double locking mechanism using rotatable levers is advantageous for quickly locking the first frame or second frame to the at least one flanges support member, while at the same time deforming the thermoplastic first sheet, respectively the thermoplastic second sheet. A first lever and a second lever stacked on each other are beneficial to limit the required volume for the double locking mechanism and consequently the potential influence of the double lock mechanism on the radiotherapy. It also limits the width, allowing the device to fit in the MRI coils.

In a preferred embodiment the second frame comprises clamps for securing the first and the second frame to the at least one flanged support member. The clamps are a specific embodiment of the previously described attachment means for attaching the first frame and the second frame to the at least one flanged support member.

The clamps are attached to a first side of the second frame. The clamps are glued, welded, screwed, bolted, riveted, or by a snap fit connection attached to the first side of the second frame. The clamps are removably attached to the at least one flanged support member. Removably attached means that the clamps can be attached and removed multiple time to the at least one flanged support member. This is beneficial for reusing the first sheet and second sheet for multiple radiotherapy sessions. The clamps preferably form a snap fit connection with the at least one flanged support member.

The first frame is positioned in between the at least one flanged support member and the second frame. By attaching the clamps to the at least one flanged support member, the second frame is secured to the at least one flanged support member and the first frame is clamped in between the second frame and the at least one flanged support member and as such secured.

Clamps are beneficial for quickly and simply securing the first frame and the second frame to the at least one flanged support member, without the use of any tools, and reducing the workload of a practitioner. Clamps are also beneficial due to the small dimensions of a clamp, resulting in a limited influence on radiation, especially in case of proton therapy.

In a further embodiment the clamp comprises a hook and the at least one flanged support member a corresponding notch for receiving the hook. A notch is beneficial compared to a protrusion and a corresponding hook because it results in a smaller total volume for the clamp compared to a hook and protrusion, again limiting the influence of the clamp on radiation.

In an embodiment the clamp comprises a hinge and a hook. The hinge is adapted for moving the hook from a first position beside the at least one flanged support member to a second position wherein the hook is attached to the at least one flanged support member. The hinge is preferably a living hinge. This embodiment is advantageous because it allows securing the second frame and the first frame to the at least one flanged support member in one simple and quick action.

In an alternative embodiment the clamp comprises a hook, shiftable between a first position and a second position. The clamp can be positioned in the first position and the second position. The first position and the second position are discrete positions. In a first position the hook is positioned beside the at least one flanged support member. In a second position the hook is attached to the at least one flanged support member. The hook is shiftable in a direction parallel to the plane formed by the second frame and the second sheet. Alternatively the hook is shiftable in a direction perpendicular to said plane. Alternatively the hook is shiftable in line with a pre-defined angle to said plane once placed on a radial part of the second frame.

Preferably the at least one flanged support member comprises a slot for shifting the hook from the first to the second position and back. Preferably the slot comprises guiding sides or rails for guiding the clamps in the slot from the first position to the second position and back. Preferably the slot or the clamp comprises a flexible projection for retaining the hook in the first or second position. The clamp respectively the slot comprises complementary recesses for receiving the projection.

Preferably the clamp comprises a retaining element for obstructing removal of the clamp from the slot. Preferably the retaining element comprises snap fit means for connecting the retaining element to the second frame.

This embodiment has similar advantages as the previously described embodiment of the clamp comprising a hinge. This embodiment has the additional advantage that it is sturdier than a hinge, allowing multiple reuses of the second frame for multiple radiotherapy sessions.

In a preferred embodiment, the second sheet comprises a cutout. The cutout results in a first strap and a second strap. The first strap and the second strap are extending from a first side of the second frame to a second side of the second frame, opposite to the first side.

This embodiment is advantageous because it leaves the patient body part visible in between the first and second strap, while the patient body part remains strongly immobilized by the first sheet, the first and the second strap. The patient body part is enclosed in the double shell mask formed by the first sheet, the first strap and the second strap. The patient body part is completely supported by the first sheet, limiting movement of the patient body part and increasing comfort for a patient. The improved visibility on the patient body part allows close monitoring of the patient body part during treatment. This is especially beneficial in case of Surface Guide Radiation Therapy (SGRT). SGRT uses stereo vision technology to track the patient body part in 3D, for both setup and motion management during radiotherapy, thereby avoiding irradiation of healthy parts of a patient's body. It is obvious that this requires visibility on the patient body part. The combination of SGRT and the strong immobilization of the patient body part reduces side effects of irradiation on healthy parts of a patient's body tremendously, for instance cardiac perfusion defects when treating left breast cancer. This embodiment is additionally beneficial when used to immobilize a patient's head. A double shell mask completely enclosing the head can cause claustrophobic feelings and may hinder breathing because the mouth and nose are covered by the second sheet. The cutout reduces the claustrophobic feelings and it makes breathing easier.

In a second aspect, the invention relates to a method for immobilization of a patient body part for radiotherapy.

In a preferred embodiment the method comprises the steps of:
  mounting a device comprising at least one flanged support member and at least one support member fixation means to a fixation surface, wherein the at least one flanged support member is mounted with the at least one support member fixation means to the fixation surface at a distance from said fixation surface, wherein the at least one flanged support member is adapted to receive and retain a first and optionally a second frame;
  mounting a first frame, comprising a first sheet, to the at least one flanged support member;
  placing the patient body part to be immobilized on the first sheet thereby covering the anatomical contours of a first area of said body part;
  optionally mounting a second frame, comprising a second sheet, on the first frame to the at least one flanged support member thereby covering the anatomical contours of a second area of said body part which is not covered by the first sheet, to form a double shell mask enclosing said body part.

The at least one flanged support member comprises at one side a curved extension towards the fixation surface, wherein the first frame or the first frame and the second frame are bent to follow the curved extension of the at least one flanged support member.

The method is adapted for supporting the immobilized body part free from the fixation surface by the two sheets and the device. This means that the immobilized body part is not in contact with the fixation surface but is separated from said surface by a distance d.

The method is advantageous because body parts close to the trunk of a patient resting on the fixation surface are immobilized with a double shell, resulting in an optimal immobilization of said body parts, e.g. neck, shoulders, upper arms and upper legs, and having a positive influence on the accuracy of radiotherapy for these body parts. Additionally advantageous about the method is that these body parts near the trunk are comfortably supported, even when immobilization of these body parts is not required for radiotherapy, causing less fatigue or discomfort in these body parts. When immobilization of these body parts is not required, the second frame and sheet can be limited to the body part that needs to be immobilized for radiotherapy.

For some therapies it is even not required that the body part receiving radiotherapy is immobilized, but only supported. In that case the use of the first frame is sufficient.

In a preferred embodiment, the first and the optional second sheets are suitable to be formed on the patient body part such as to conform the anatomical contours of said patient body part. The first and the optional second sheet are preferably thermoplastic sheets. The embodiment comprises the additional steps of heating the first sheet and the second sheet before mounting the first frame to the at least on flanged support member, deforming the thermoplastic first sheet conform the anatomical contours of the first area of said body part after placing the patient body part to be immobilized on the first sheet, cooling the thermoplastic first sheet to ambient temperature to rigidify the deformed first moldable thermoplastic sheet, deforming the thermoplastic second sheet while mounting the second frame to the at least on flanged support member and cooling the thermoplastic second sheet to ambient temperature to rigidify the deformed second moldable thermoplastic sheet. The patient remains in the same position during the production of the double shell mask. This means that, for mounting the second thermoplastic sheet, the patient is maintained in the same position as for mounting the first thermoplastic sheet. This embodiment is beneficial because a double shell that closely matches the anatomic contours of the patient's body part can be formed without a lot of preparation.

In another preferred embodiment, the first and the optional second sheets are preformed sheets which are conform to the anatomical contours of the patient body part. The method according to an embodiment of the invention can further comprise the step of scanning the body part for preforming the first and the optional second sheets. This embodiment is beneficial because the patient is not required to lay still until thermoplastic sheets are cured as in a previous described embodiment.

In a preferred embodiment, when the patient body part to be immobilized is placed on a heated thermoplastic first sheet, a pressure is applied on said body part. The pressure is applied such as to conform the first sheet to the anatomical contours of a first area of the patient body part. Said pressure should be applied with care as it should high enough to conform the sheet to the body part and simultaneously, it should not be too high to avoid bringing the patient body part in contact with the fixation surface. The thermoplastic first sheet has a low elasticity to avoid that the patient body part contacts the fixation surface.

In a preferred embodiment, the heated second thermoplastic sheet is only brought in contact with the patient's body part without pressing it against said body part. The second sheet is provided with high elasticity such as it conforms the patient's body part anatomical contours without pressure requirement. In some cases and wherein the face is covered by the second sheet, it might be required to apply a pressure on the bone of the nose to conform the sheet to the nose of the patient. The use of a thermoplastic first sheet with a low elasticity compared to the elasticity of the thermoplastic second sheet is advantageous because the body part can be supported free from the fixation surface without use of cushions or other support blocks.

In a preferred embodiment, when mounted on the device, the thermoplastic first sheet of the first frame is not supported in its central region but is only circumferentially supported by the first frame and the at least one flanged support member. This is achievable as the thermoplastic first sheet has a rigidity that allows providing a sufficient force to support said body part, e.g. head, neck, shoulders, upper arms or legs, and simultaneously providing a sufficient elasticity such as to deform the sheet according to the anatomical contours of said body part. After cooling, the cured thermoplastic first sheet will be separated from the fixation surface or a base plate of the device by an open accessible space. Said open accessible space is created underneath the cured thermoplastic first sheet. The cured thermoplastic first sheet will not be in contact with the fixation surface or a base plate of the device. This is advantageous as the thermoplastic sheet will deform according to only and solely the patient's body part. In addition, the practitioner will have access and will be able to touch, support and shape the thermoplastic sheet when the patient's head is placed on the other surface of the sheet. The practitioner can than make sure that the sheet is perfectly matching the anatomical contours of the head, including relevant reference points like occipital bone structures, collarbones and vertebrae.

In a preferred embodiment, the thermoplastic first and the optional second sheets are heated at a temperature comprised between 70 and 90° C., preferably between 65 and 85° C. The sheets may be softened by warming them to a temperature above their glass transition temperature, for instance by immersion in warm water, at which temperature they become shapeable.

In a preferred embodiment, the sheets are warmed by immersion in an aqueous liquid having a temperature comprised between 70-90° C. As described above, the sheets are allowed to cool below their glass transition temperature, preferably to ambient temperature of 20° C. to 30° C. The sheets will rigidify and provide a form-fitting double shell mask.

In a preferred embodiment, the first frame or the first frame and the second frame are flat before initial use and comprise at least at one side a deformable part. The deformable part is preferably at the side of the patient's trunk. The deformable part is being deformed in a direction transverse to the fixation surface to follow the curved extension of the at least one flanged support member.

This embodiment is advantageous because the first frame and the second frame require less space for storage before initial use. This is additionally advantageous because the first frame and the second frame can be used with different types of flanged support members, which comprise curved extensions with different angles towards the fixation surface. By deforming the deformable part, the first frame and the second frame can be easily adapted to the corresponding angle of the curved extension.

In a preferred embodiment the first frame and the second frame are secured to the at least one flanged support member by removably attaching clamps to the at least one flanged support member. Removably attached means that the clamps can be attached and removed multiple time to the at least one flanged support member. This is beneficial for reusing the first sheet and second sheet for multiple diagnostic and radiotherapy sessions. The clamps preferably form a snap fit connection with the at least one flanged support member. The clamps are attached to a first side of the second frame. By attaching the clamps to the at least one flanged support member, the second frame is secured to the at least one flanged support member. The first frame is positioned in between the at least one flanged support member and the second frame. The first frame is clamped in between the second frame and the at least one flanged support member and as such secured.

This embodiment is beneficial for quickly and simply securing the first frame and the second frame to the at least one flanged support member, without the use of any tools, while reducing the workload of a practitioner. Clamps are also beneficial due to the small dimensions of a clamp, resulting in a limited influence on radiation.

In a preferred embodiment the first frame is locked to the device by rotating a first rotatable lever of a double locking mechanism from a first position to a second position. The second frame is locked to the device by rotating a second rotatable lever of the double locking mechanism from a first position to a second position. The first rotatable lever and the second rotatable lever are stacked on each other.

This embodiment is especially advantageous for attaching the first frame and the second frame on the curved extension of the at least one flanged support member in combination with thermoplastic sheets and with first frames or first frames and second frames comprising a deformable part. When deforming the thermoplastic first sheet or the thermoplastic second sheet to anatomical contours of said body part, pressure is applied to the first sheet or the second sheet, consequently also resulting in forces on the first frame, respectively the second frame. These forces could cause deformation of the deformable part of the first frame, respectively the second frame in a direction away from the fixation surface. The double lock mechanism allows for already attaching the first frame and subsequently the second frame to the at least one flanged support member before both the first frame and the second frame are installed and attached on the at least one flanged support member. A double locking mechanism using rotatable levers is advantageous for quickly locking the first frame or second frame to the at least one flanges support member, while at the same time deforming the thermoplastic first sheet, respectively the thermoplastic second sheet. A first lever and a second lever stacked on each other are beneficial to limit the required volume for the double locking mechanism and consequently the potential influence of the double lock mechanism on the radiotherapy.

In a preferred embodiment, the second sheet comprises a cutout. The cutout results in a first strap and a second strap. The first strap and the second strap are extending from a first side of the second frame to a second side of the second frame, opposite to the first side. The first strap and the second strap immobilize the patient body part, leaving the patient body part visible in between the first strap and the second strap.

The patient body part is enclosed in the double shell mask formed by the first sheet, the first strap and the second strap. The patient body part is completely supported by the first sheet, limiting movement of the patient body part and increasing comfort for a patient. The improved visibility on the patient body part allows close monitoring of the patient body part during treatment. This is especially beneficial in case of Surface Guide Radiation Therapy (SGRT). This embodiment is additionally beneficial when used to immobilize a patient's head. A double shell mask completely enclosing the head can cause claustrophobic feelings and may hinder breathing because the mouth and nose are covered by the second sheet. The cutout reduces the claustrophobic feelings and it makes breathing easier.

In a third aspect, the invention relates to a kit for immobilization of a patient body part for radiotherapy applications.

In a preferred embodiment the kit comprises:
a device, comprising at least one flanged support member and at least one support member fixation means for mounting the at least one flanged support member to a fixation surface at a distance from said fixation surface;
a first frame, comprising a first sheet, wherein the first frame forms a circumferential rim for the first sheet;
optionally a second frame, comprising a second sheet, wherein the second frame forms a circumferential rim for the second sheet, wherein the second frame is superimposable on the first frame.

The at least one flanged support member comprises at one side a curved extension towards the fixation surface.

A kit according to the current embodiment provides an advantageous effect that with a limited number of elements and without a high workload for the practitioner a body part of a patient can be comfortably and optimally immobilized with a double shell, even when the body part is close to the trunk of the patient.

In case the body part receiving radiotherapy only needs to be supported, only the first frame is required.

In a preferred embodiment the first frame or the first frame and the second frame are flat and comprise at least at one side a deformable part, wherein the deformable part is deformable in a direction transverse to the fixation surface.

This embodiment is beneficial because the first frame and the second frame of the kit require less space for storage before initial use. This is additionally advantageous because the first frame and the second frame can be used with different types of flanged support members, which comprise curved extensions with different angles towards the fixation surface.

In a preferred embodiment the kit further comprises clamps for securing the first frame and the second frame to the at least one flanged support member. Clamps are beneficial for quickly and simply securing the first frame and the second frame to the at least one flanged support member, without the use of any tools, while reducing the workload of a practitioner. Clamps are also beneficial due to the small dimensions of a clamp, resulting in a limited influence on radiation.

In a preferred embodiment, the second sheet comprises a cutout, resulting in a first strap and a second strap. The first strap and the second strap are extending from a first side of the second frame to a second side of the second frame, opposite to the first side.

The first strap and the second strap are suited to immobilize the patient body part, leaving the patient body part visible in between the first strap and the second strap.

The improved visibility on the patient body part allows close monitoring of the patient body part during treatment. This is especially beneficial in case of Surface Guide Radiation Therapy (SGRT). This embodiment is additionally beneficial when the kit is used to immobilize a patient's head. A double shell mask completely enclosing the head can cause claustrophobic feelings and may hinder breathing because the mouth and nose are covered by the second sheet. The use of the first strap and the second strap reduces the claustrophobic feelings and it makes breathing easier.

In a fourth aspect, the invention relates to a device for immobilization of a patient body part for radiotherapy applications.

In a preferred embodiment the device comprises at least one flanged support member and at least one support member fixation means for mounting the at least one flanged support member to a fixation surface at a distance from said fixation surface. The at least one flanged support member is adapted to receive and retain a first and optionally a second frame. The at least one flanged support member comprises at one side a curved extension towards the fixation surface. The curved extension is adapted to retain the first frame or the first frame and the second frame. The at least one flanged support member comprises preferably attachment means for attaching the first frame and the optional second frame to the at least one flanged support member. The curved extension comprises preferably attachment means for attaching the first frame and the optional second frame to the curved extension. Non-limitative examples are openings for receiving rivets, screws or bolts and snap fit means connections.

This embodiment is advantageous because also body parts close to the trunk of a patient resting on the fixation surface can be immobilized with a double shell mask, because a first frame and a second frame that are bent towards the fixation surface, can be attached to the curved extension, firmly positioning the first frame and the second frame next to body parts near the trunk of the patient. This results in an optimal immobilization of said body parts and a positive influence on the accuracy of radiotherapy for these body parts.

In case the body part receiving radiotherapy only needs to be supported, only the first frame is required. Body parts near the trunk are comfortably supported, causing less fatigue or discomfort in these body parts and also avoiding pressure points.

A person of ordinary skill in the art will appreciate that a system according to the first aspect is by preference configured to execute a method according to the second aspect, that a method according to the second aspect is executed by preference using a system according to the first aspect, that a kit according to the third aspect is adapted for making a system of the first aspect and that a system according to the first aspect comprises by preference a device according to the fourth aspect. Any feature described in this document, both above and below, can therefore relate to any of the four aspects of the present invention.

The invention is further described by the following non-limiting figures which further illustrate the invention, and are not intended to, nor should they be interpreted to, limit the scope of the invention.

DESCRIPTION OF FIGURES

Figure 1B:
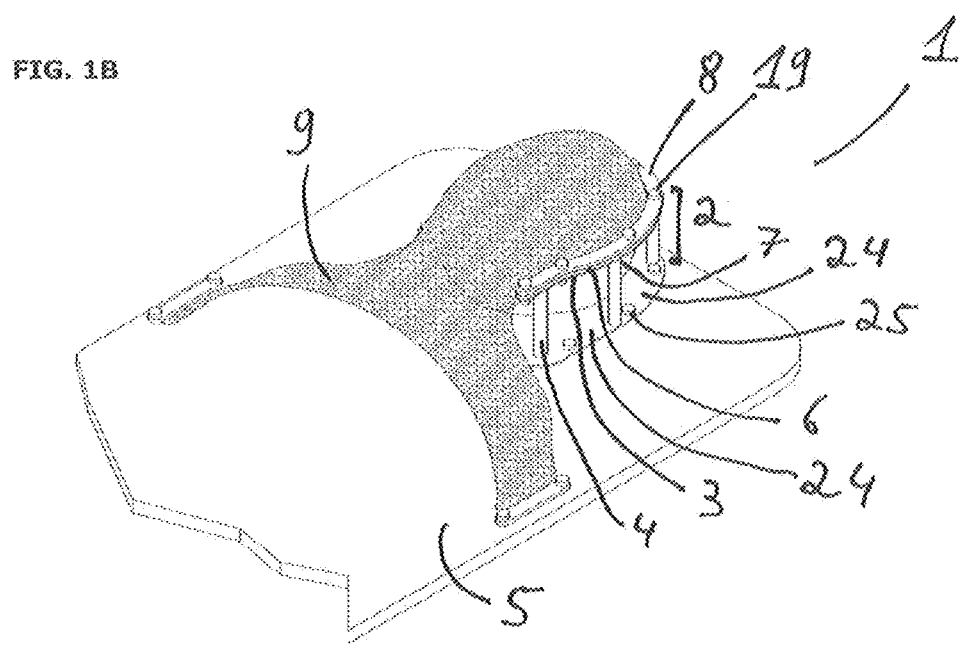
FIG. 1B shows a three-dimensional representation of the same system as in FIG. 1A in assembled state.
Figure 1C:
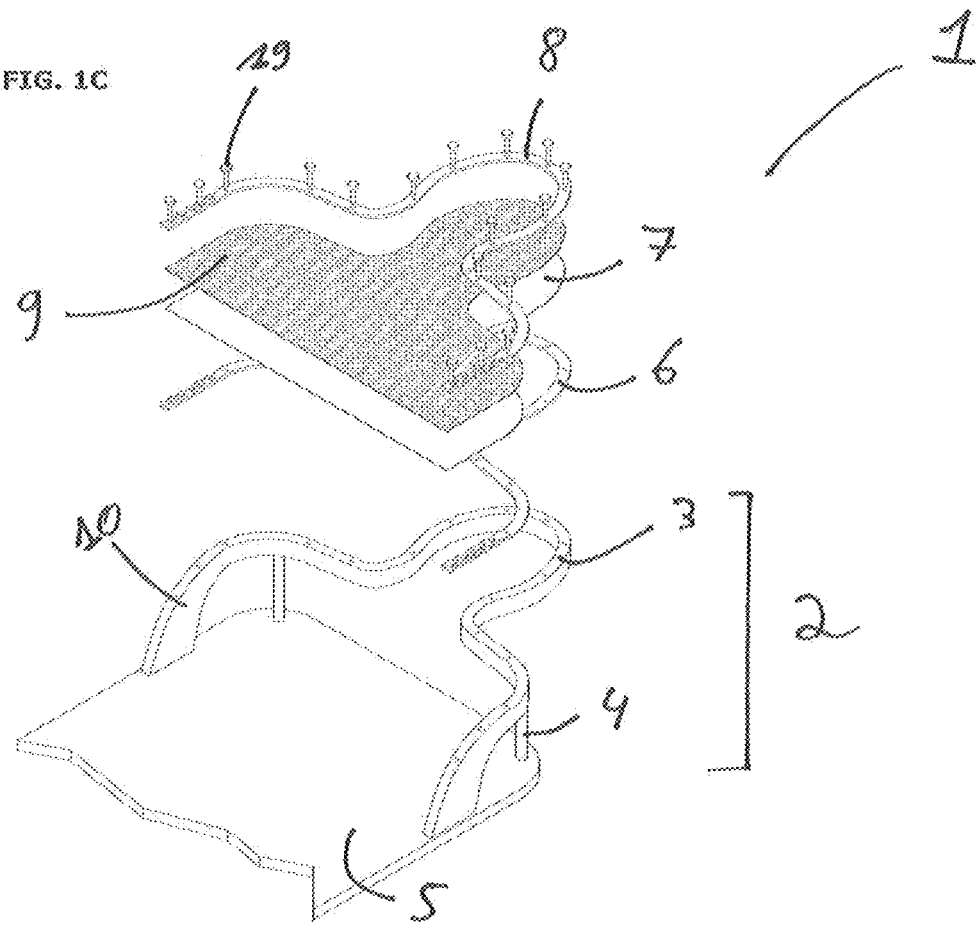
FIG. 1C shows an exploded-view of a system according to an embodiment of the current invention.
Figure 1D:
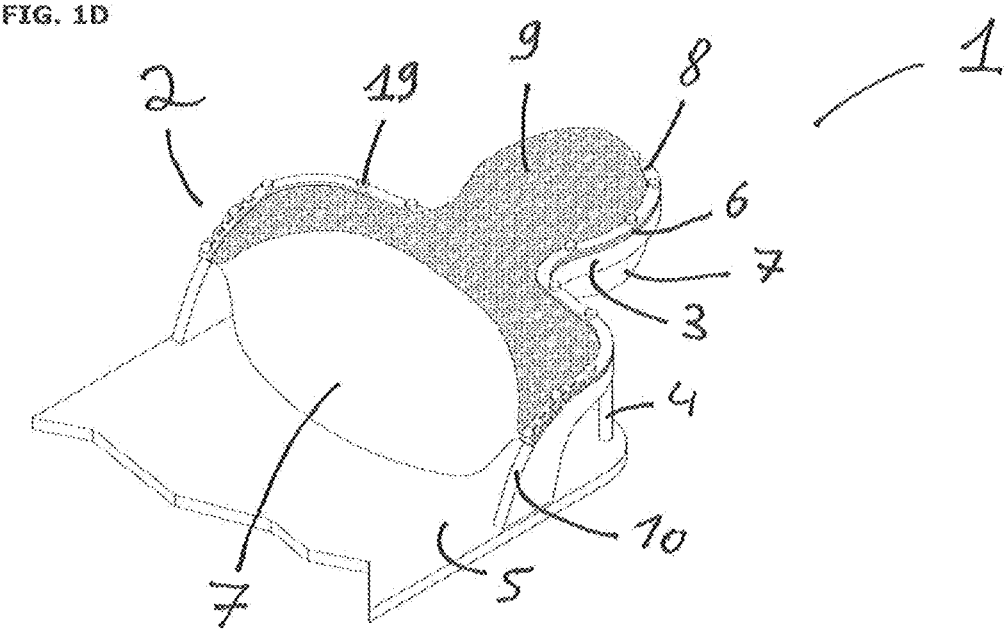
FIG. 1D shows a three-dimensional representation of the same system as in FIG. 1C in assembled state.

FIG. 1A shows an exploded-view of a system according to the prior art. The system (1) comprises a device (2), a first frame (6) with a first sheet (7), a second frame (8) with a second sheet (9) and attachment means (19) for attaching the first frame (6) and the second frame (8) to the device (2). The first frame (6) and the second frame (8) are superimposed on each other and are supported by a flanged support member (3) of the device (2). The flanged support member (3) is not directly fixated by the support member fixation means (4) to a fixation surface (5), but is first fixated by the support member fixation means (4) to a base plate (24). The base plate (24) is fixated to the fixation surface (5) using fixation means (25). The first sheet (7) and the second sheet (9) are thermoplastic sheets. The first sheet (7) and the second sheet (9) are shown before initial use and are still flat. FIG. 1B shows a three-dimensional representation of the same system as in FIG. 1A in assembled state. The first sheet (7) is molded and formed for covering anatomical contours of head and neck and the second sheet (9) is molded and formed for covering anatomical contours of the head, neck and shoulders which is not covered by the first sheet (7). The first sheet (7) and the second sheet (9) form a double shell mask enclosing the head. As can be clearly seen, the first sheet (7) does not support the shoulders, leading to suboptimal immobilization of the shoulders and neck, what has an adverse influence on radiotherapy for these body parts. Another disadvantage of this system is that it could cause fatigue or discomfort in the shoulders and neck. FIG. 1C shows an exploded-view of a system according to an embodiment of the current invention. The setup of the system is very similar as the system according to the prior art. The important difference is that the flanged support member (3) comprises at a side near the patient's trunk a curved extension (10) towards the fixation surface (5). The curved extension (10) touches the fixation surface (5). The system is shown before initial use, so the first frame (6) with the first sheet (7) and the second frame (8) with the second sheet (9) are still flat. FIG. 1D shows a three-dimensional representation of the same system as in FIG. 1C in assembled state. The first frame (6) and the second frame (8) are bent to follow the curved extension (10) of the flanged support member (3). The first sheet (7) is molded and formed for covering anatomical contours of head, neck and shoulders and the second sheet (9) is molded and formed for covering anatomical contours of the head, neck and shoulders which is not covered by the first sheet (7). The first sheet (7) and the second sheet (9) form a double shell mask enclosing the head, neck and shoulders, leading to an optimal immobilization of the head, neck and shoulders. The patient is comfortable as also the neck and shoulders are supported.

Figure 2A:
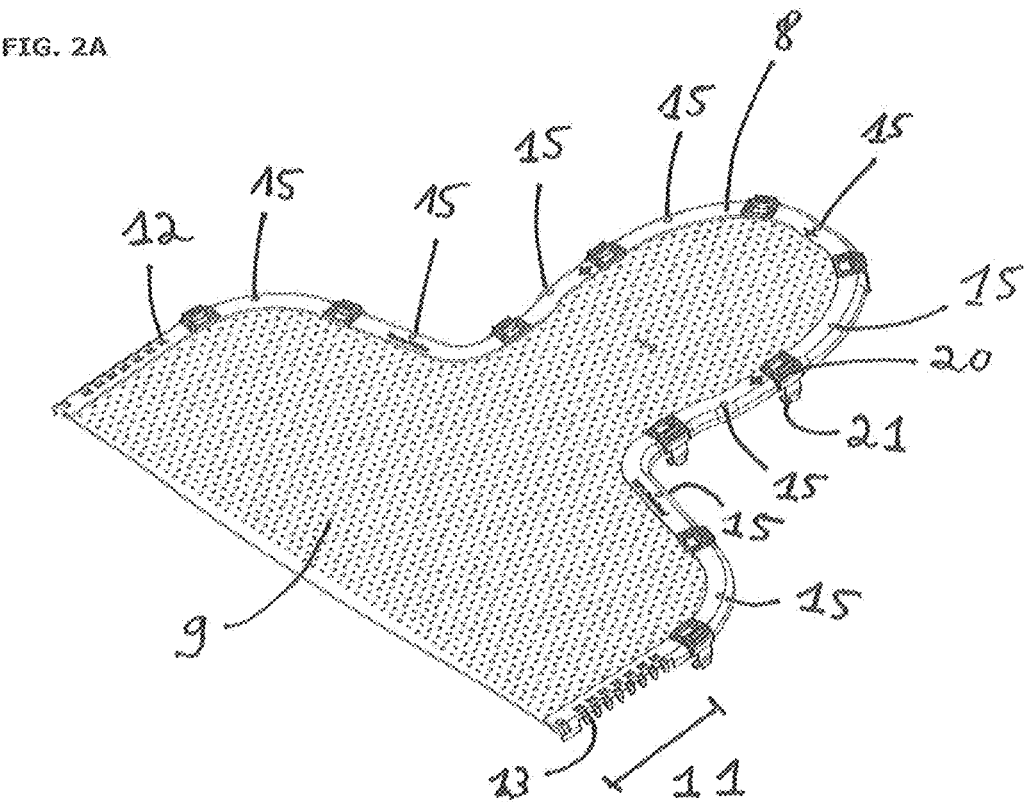
FIG. 2A shows a three-dimensional representation of a second frame for head and shoulder immobilization according to an embodiment of the current invention.
Figure 2B:
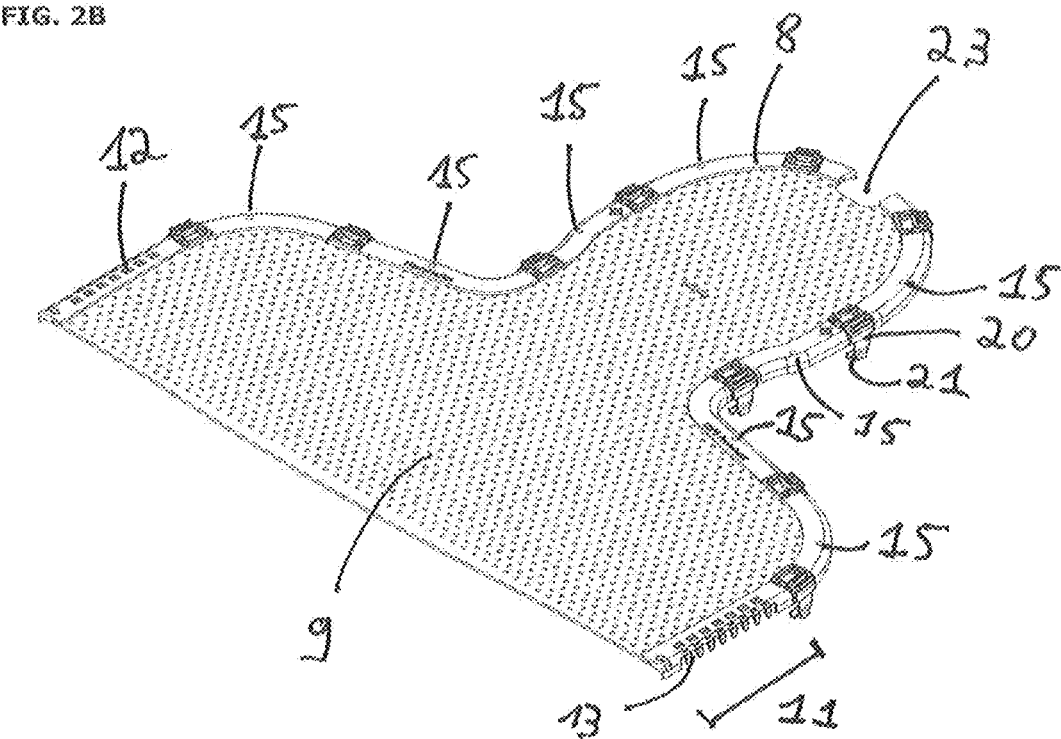
FIG. 2B shows a three-dimensional representation of a similar second frame, adapted for long-haired people.

FIG. 2A shows a three-dimensional representation of a second frame for head and shoulder immobilization according to an embodiment of the current invention. The second frame (8) comprises a second sheet (9). The second sheet (9) is a thermoplastic sheet. The second frame (8) is shown before initial use, so the second frame (8) and the second sheet (9) are still flat. The second frame (8) comprises at a side near the patient's trunk a deformable part (11). The second frame (8) comprises positioning means (12) for positioning the second sheet (9) in the second frame (8). The positioning means (12) are on the deformable part (11) open and separated protrusions. The second frame (8) comprises guiding means (13) for guiding the second frame (8) to a correct position on a first frame (6). The guiding means (13) are on the deformable part (10) separated protrusions. The second frame (8) comprises clamps (20) for securing a first frame (6) and the second frame (8) to a flanged support member (3). The clamps (20) comprise a hook (21). The second frame (8) comprises protrusions (15). These protrusions (15) are received in hollow protrusions (15) of a first frame (6). This is beneficial to avoid that the first frame (6) and the second frame (8) can rotate or shift in the plane of the surface of a flanged support member (3). FIG. 2B shows a three-dimensional representation of a similar second frame, adapted for long-haired people. The second frame (8) and the second sheet (9) comprise a cutout for hair (23) to pass for instance a pony tail. This avoids that long hair hinders forming a double shell mask.

Figure 3A:
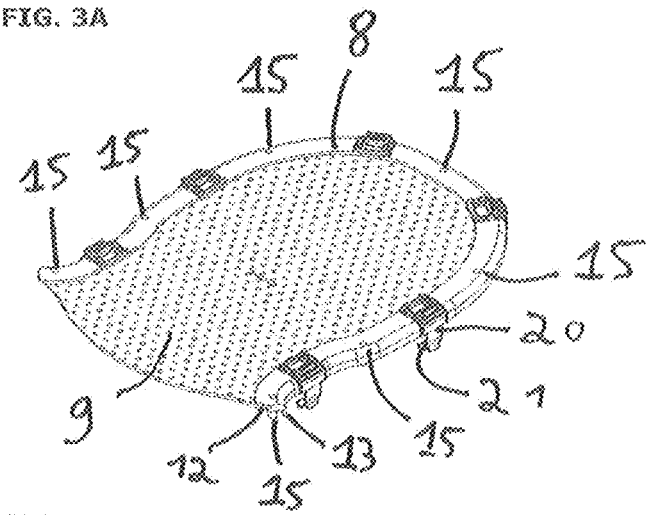
FIG. 3A shows a three-dimensional representation of a second frame for head immobilization according to an embodiment of the current invention.
Figure 3B:
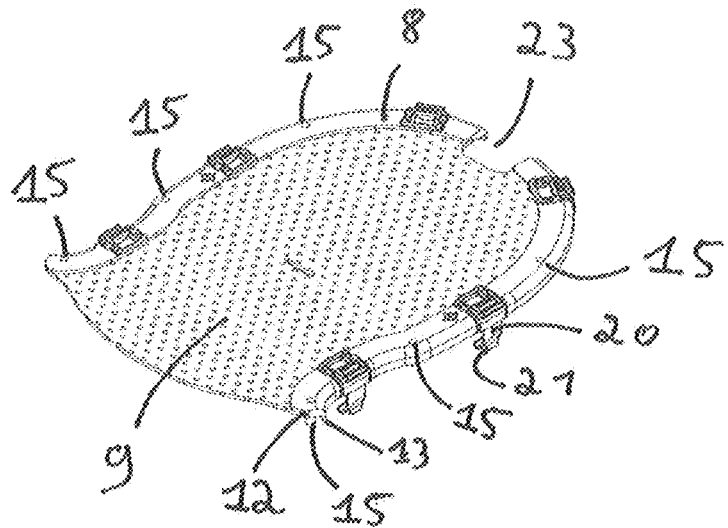
FIG. 3B shows a three-dimensional representation of a similar second frame, adapted for long-haired people.

FIG. 3A shows a three-dimensional representation of a second frame for head immobilization according to an embodiment of the current invention and FIG. 3B shows a three-dimensional representation of a similar second frame, adapted for long-haired people. These second frames (8) are very similar to the second frames (8) of FIGS. 2A and 2B, but do not comprise a deformable part (11). The positioning means (12) is a ridge of a circumferential rim for the second sheet (9) formed by the second frame (8). The guiding means (13) is a raised edge at an outer circumference of the second frame (8). The second frames (8) of FIGS. 3A and 3B are compatible with a flanged support member (3) according to the current invention, but do not enclose in this case the neck and shoulders.

Figure 4:
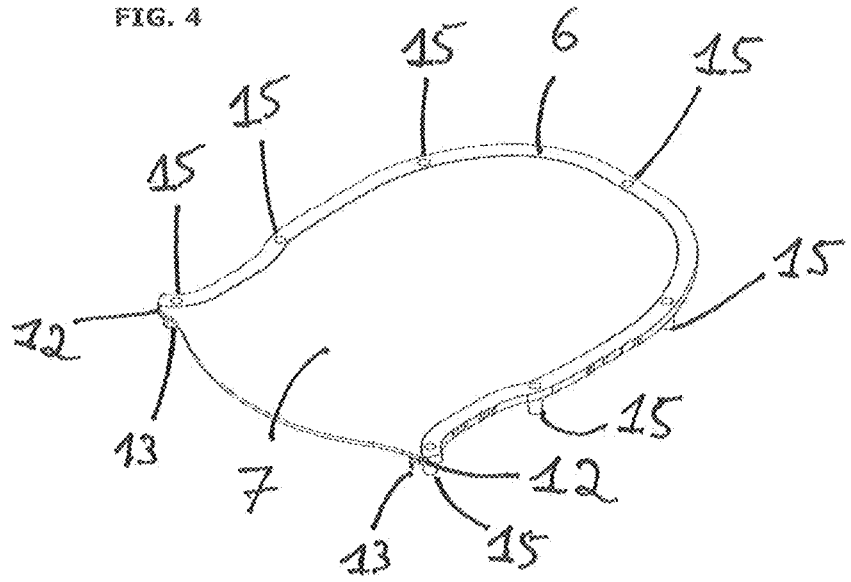
FIG. 4 shows a three-dimensional representation of a first frame for head immobilization according to an embodiment of the current invention.

FIG. 4 shows a three-dimensional representation of a first frame for head immobilization according to an embodiment of the current invention. The first frame (6) comprises a first sheet (7). The first sheet (7) is a thermoplastic sheet. The first frame (6) is shown before initial use, so the first frame (6) and the first sheet (7) are still flat. The first frame (6) comprises hollow protrusions (15) for receiving protrusions of a second frame (8). The hollow protrusions (15) are received in openings (14) of a flanged support member (3). This is beneficial to avoid that the first frame (6) and the second frame (8) can rotate or shift in the plane of the surface of the flanged support member (3). The first frame (6) does not comprise a deformable part (11). The positioning means (12) is a ridge of a circumferential rim for the first sheet (7) formed by the first frame (6). The guiding means (13) is a raised edge at a circumference of the first sheet (7)

of the first frame (6). The first frame (6) is compatible with a flanged support member (3) according to the current invention, but does not support in this case the neck and shoulders.

Figure 5C:
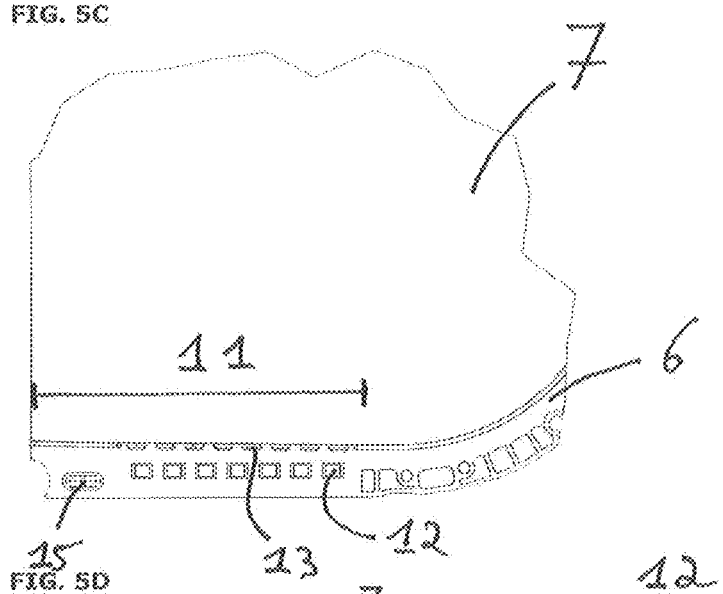
FIG. 5C shows a detail of the bottom view of FIG. 5A.
Figure 5D:
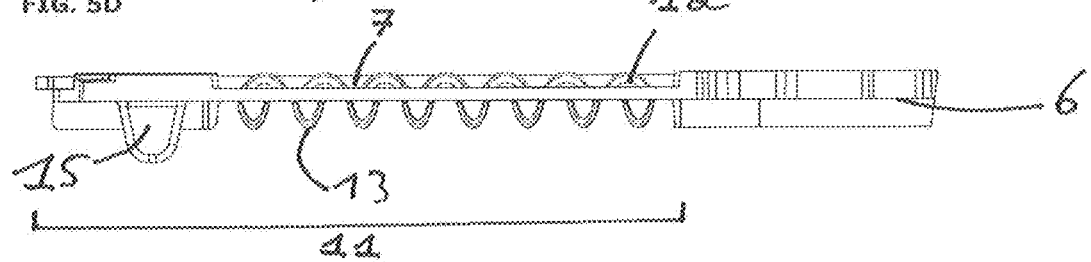
FIG. 5D shows a detail of a side view of the first frame of FIG. 5A.

FIG. 5A shows a top view of a first frame for head and shoulder immobilization according to an embodiment of the current invention. The first frame (6) is very similar to the first frame (6) of FIG. 4, but does further comprise a deformable part (11). The first frame (6) and the first sheet (7) do support head, neck and shoulders. The guiding means (13) are not visible on this figure. The positioning means (12) are on the deformable part (11) open and separated protrusions. The deformable part (11) comprises at least one protrusion (15). FIG. 5B shows a cross section of the first frame of FIG. 5A along the line AA. It is clearly visible that the guiding means (13) are on the deformable part (11) separated protrusions. It is also clearly visible that the positioning means (12) are on the deformable part (11) open and separated protrusions. The positioning means (12) are part of a corrugated surface. The protrusion (15) on the deformable part (11) is hollow. FIG. 5C shows a detail of a bottom view of the first frame in FIG. 5A. The positioning means (12) are visible on the deformable part (11) as openings of open and separated protrusions, extending from the top side of the first frame (6). The guiding means (13) are located at a circumference of the first sheet (7) of the first frame (6). FIG. 5D shows a detail of a side view of the first frame of FIG. 5A.

Figure 6A:
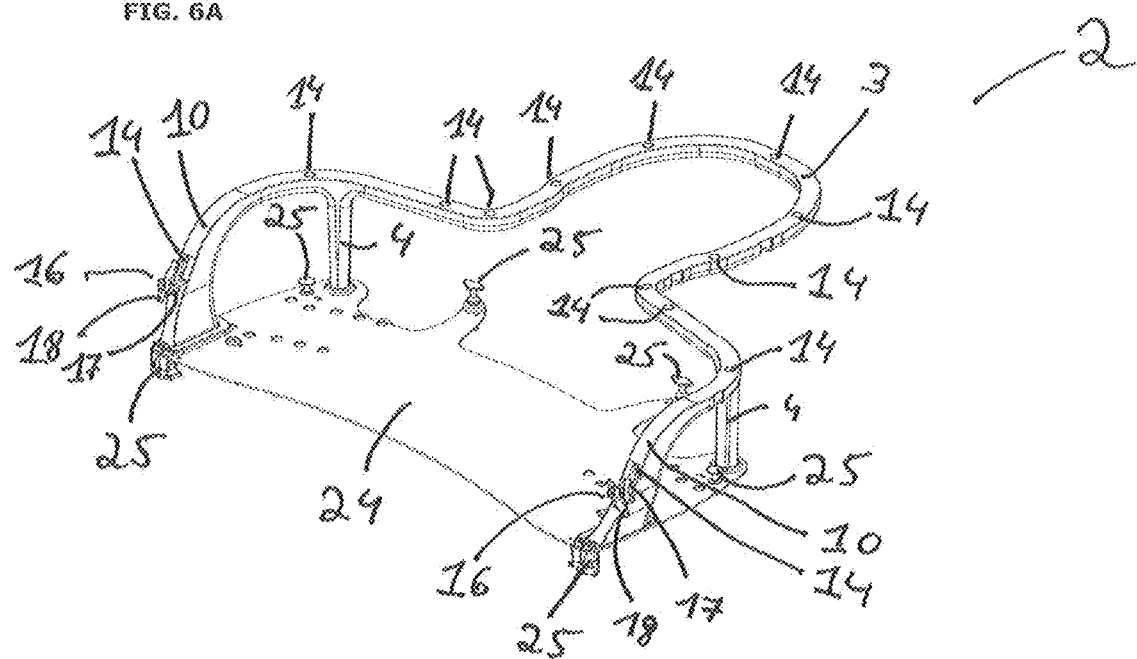
FIG. 6A shows a three-dimensional representation of a device according to an embodiment of the current invention.
Figure 6D:
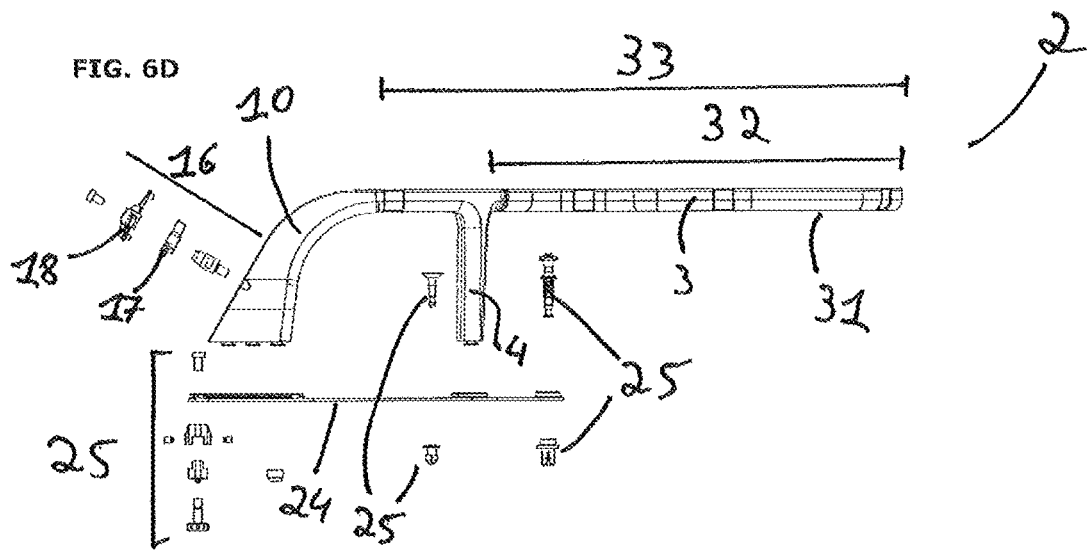
FIG. 6D shows an exploded side view of the device of FIG. 6A.

FIG. 6A shows a three-dimensional representation of a device according to an embodiment of the current invention. The device (2) has a very similar setup as the device of FIG. 1C. The flanged support member (3) comprises multiple openings (14) for receiving protrusions (15) of a first frame (6). Also the curved extension (10) comprises two openings (14) for receiving protrusions (15) of a first frame (6). The device (2) comprises further a double locking mechanism (16), comprising a first rotatable lever (17) and a second rotatable lever (18). The double locking mechanism will be explained in more detailed in FIGS. 12A-12F. The flanged support member (3) is fixated to a base plate (24) by support member fixation means (4). The base plate (24) comprises attachment means (25) for fixating the base plate to a fixation surface (5). The flanged support member (3) is indirectly fixated by the support member fixation means (4) to a fixation surface (5). The attachment means (25) are a type of twist locks. The base plate (24) is adapted for a specific type of fixation surface (5). FIG. 6B shows a side view of the device of FIG. 6A. The device has a cantilevered part (31). The length (32) of the cantilevered part (31) is at least 50% of the total length (33) of the flanged support member (3). FIG. 6C shows an exploded three-dimensional representation of the device of FIG. 6A. FIG. 6D shows an exploded side view of the device of FIG. 6A.

Figure 7A:
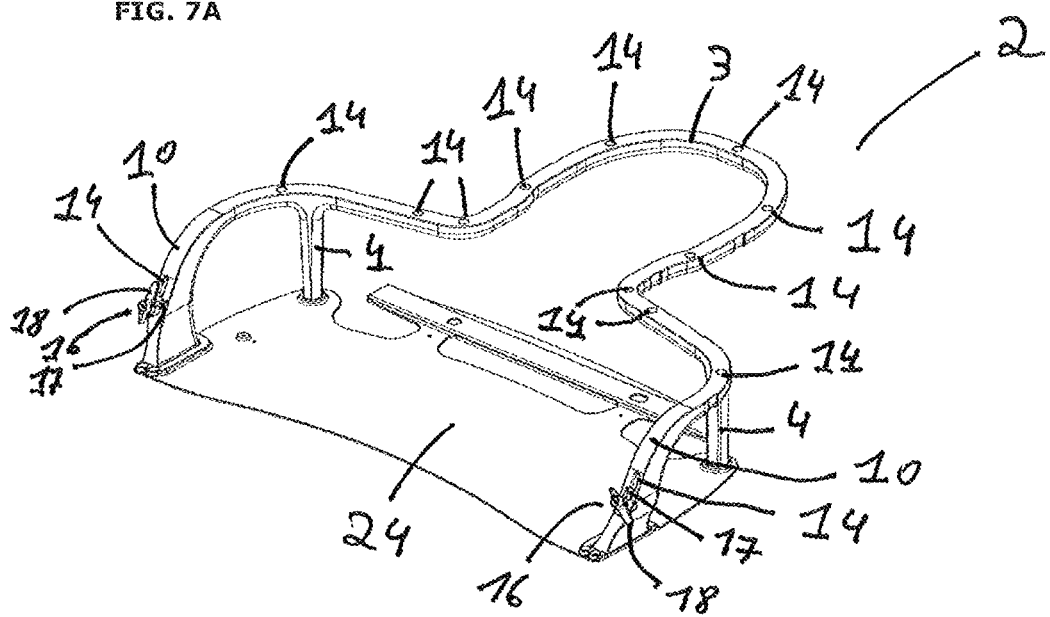
FIG. 7A shows a three-dimensional representation of an alternative device according to an embodiment of the current invention.
Figure 7B:
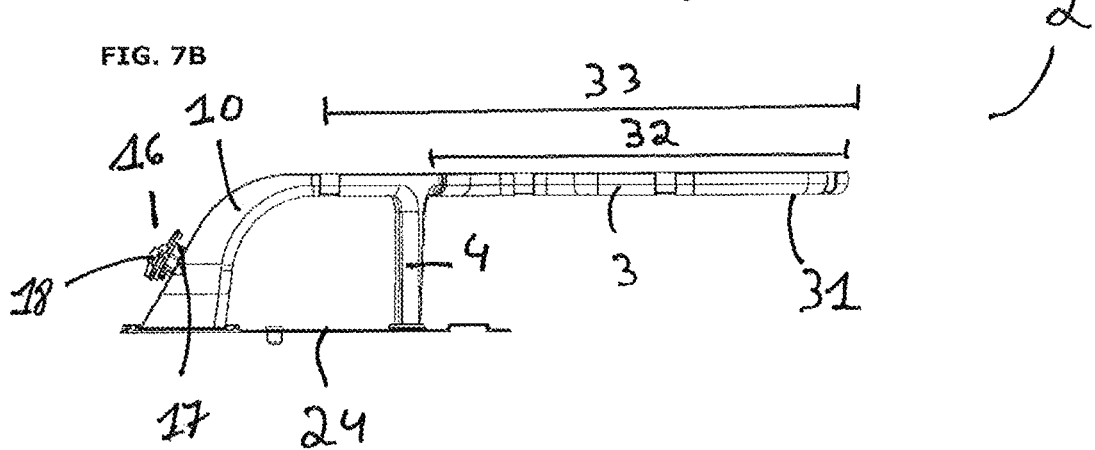
FIG. 7B shows a side view of the device of FIG. 7A.

FIG. 7A shows a three-dimensional representation of an alternative device according to an embodiment of the current invention. The device (2) has a very similar setup as the device of FIG. 6A. The base plate (24) is adapted for a second specific type of fixation surface (5). The base plate (24) does comprise openings for fixating the device (1) to the second specific type of fixation surface (5). The base plate (24) offers space at a part closest to the cranial for a lock bar with two or three fixation pivots, fitting in two or three holes or slots in this part of the base plate (24). FIG. 7B shows a side view of the device of FIG. 7A. FIG. 7C shows an exploded three-dimensional representation of the device of FIG. 7A. FIG. 7D shows an exploded side view of the device of FIG. 7A.

FIG. 8A shows a three-dimensional representation of another alternative device according to an embodiment of the current invention. The device (2) has a very similar setup as the device of FIG. 6A. The base plate (24) is adapted for a third specific type of fixation surface (5). FIG. 8B shows a side view of the device of FIG. 8A. FIG. 8C shows an exploded three-dimensional representation of the device of FIG. 8A. FIG. 8D shows an exploded side view of the device of FIG. 8A.

Figure 9A:
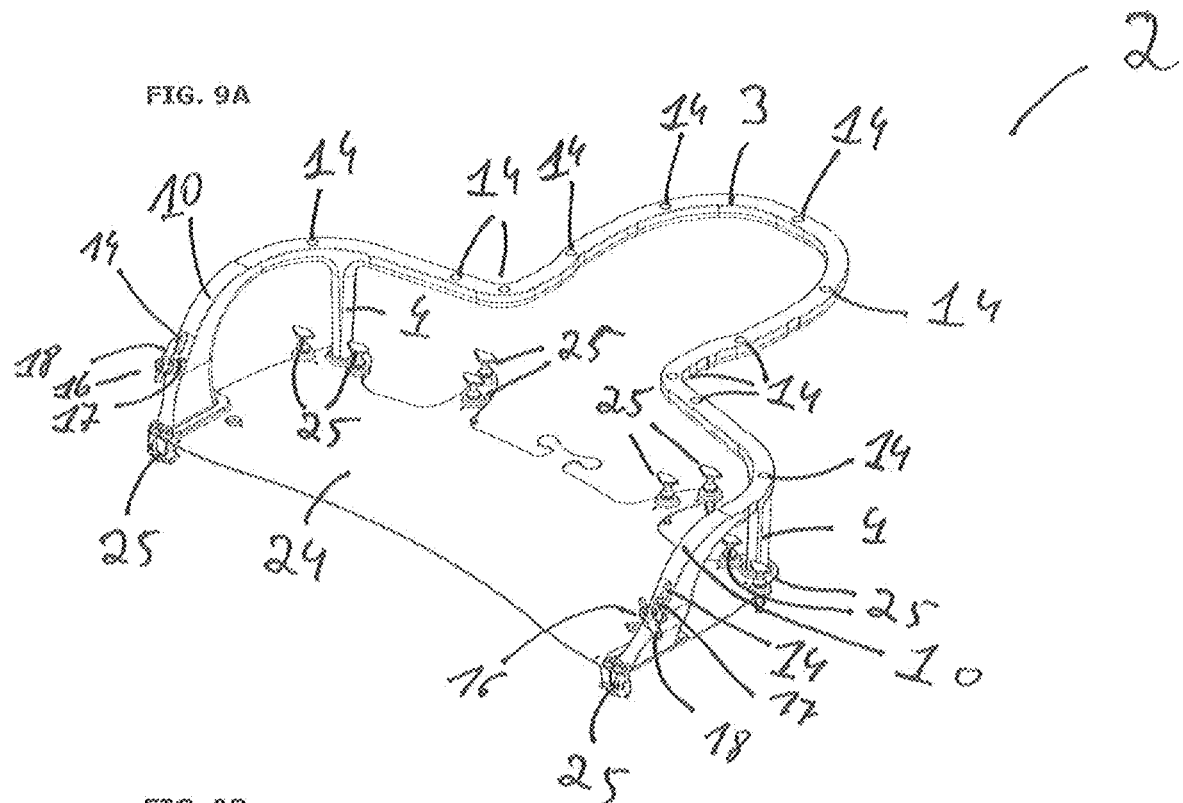
FIG. 9A shows a three-dimensional representation of yet another alternative device according to an embodiment of the current invention.
Figure 9B:
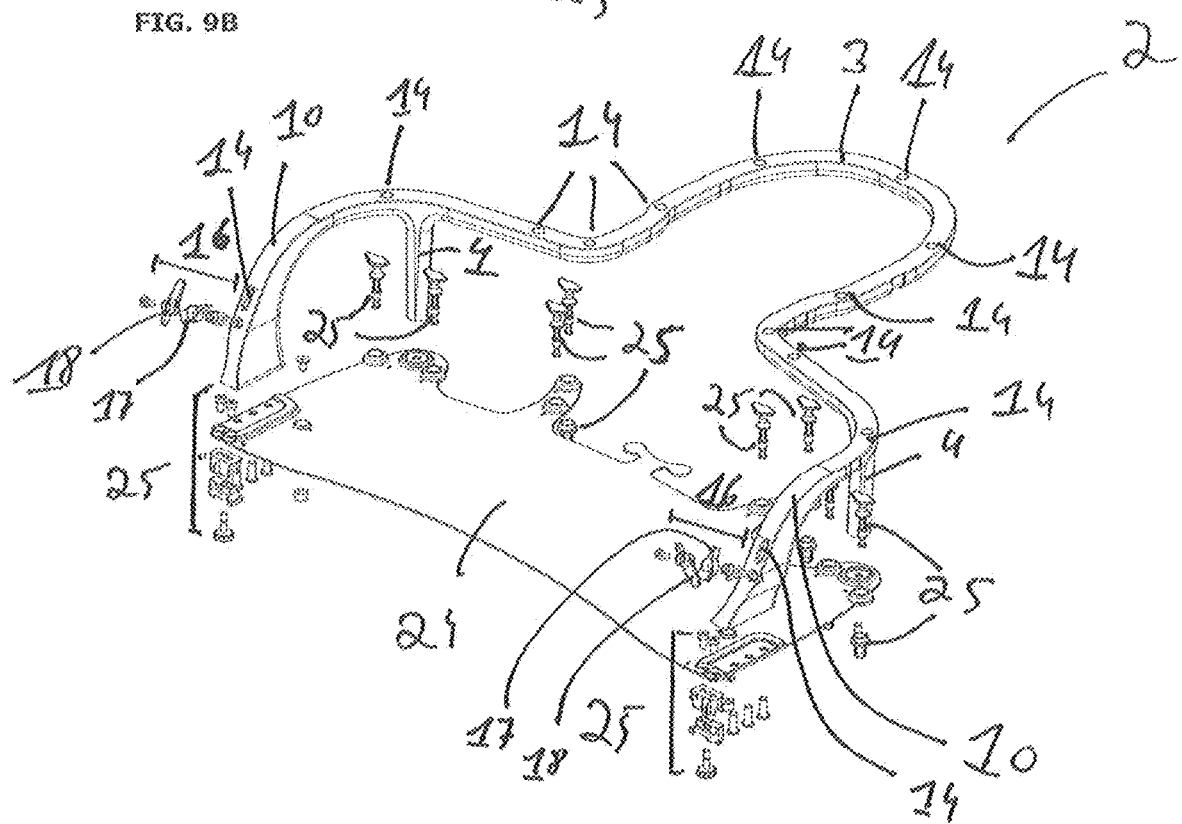
FIG. 9B shows an exploded three-dimensional representation of the device of FIG. 9A.
Figure 9C:
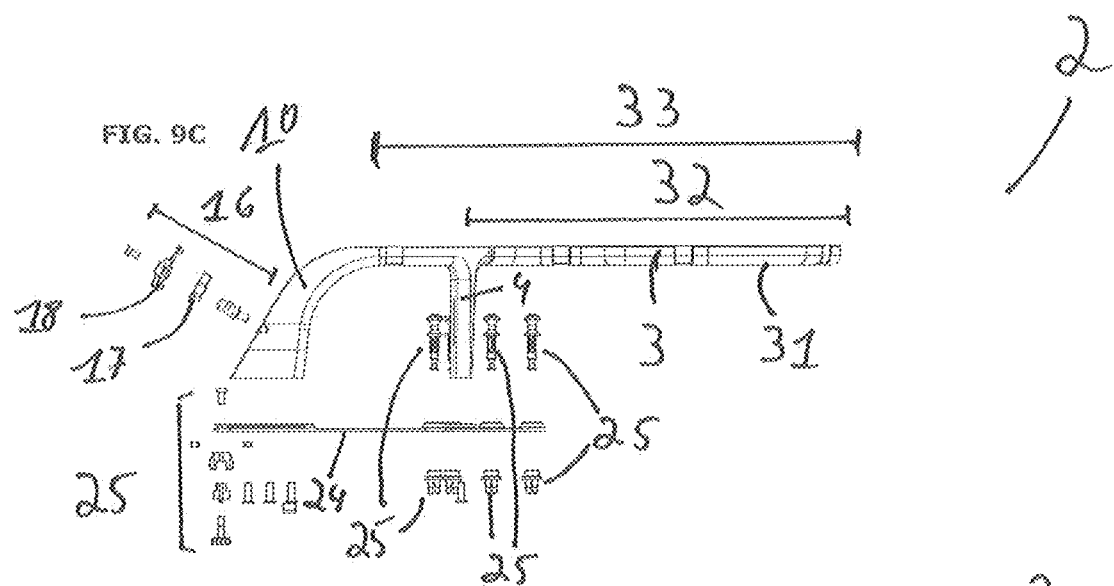
FIG. 9C shows an exploded side view of the device of FIG. 9A.

FIG. 9A shows a three-dimensional representation of yet another alternative device according to an embodiment of the current invention. The device (2) has a very similar setup as the device of FIG. 6A. The base plate (24) is adapted for a fourth specific type of fixation surface (5). FIG. 9B shows an exploded three-dimensional representation of the device of FIG. 9A. FIG. 9C shows an exploded side view of the device of FIG. 9A.

Figure 10A:
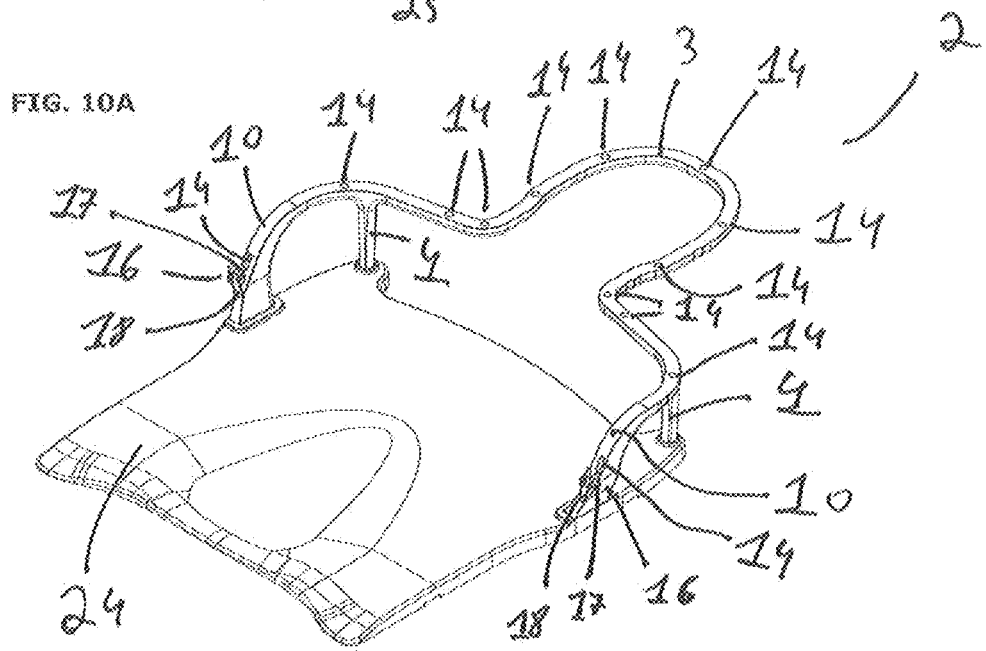
FIG. 10A shows a three-dimensional representation of even another alternative device according to an embodiment of the current invention.
Figure 10B:
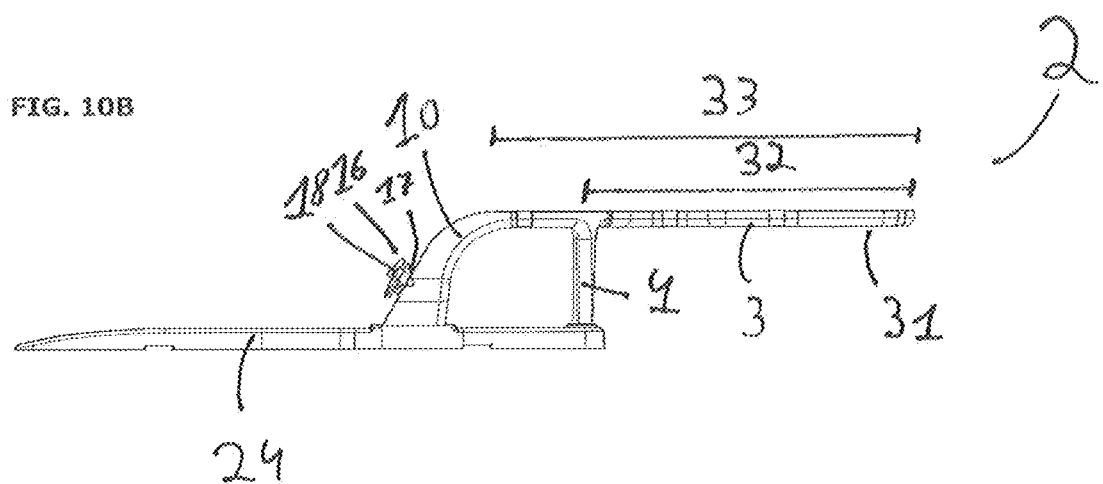
FIG. 10B shows a side view of the device of FIG. 10A.
Figure 10E:
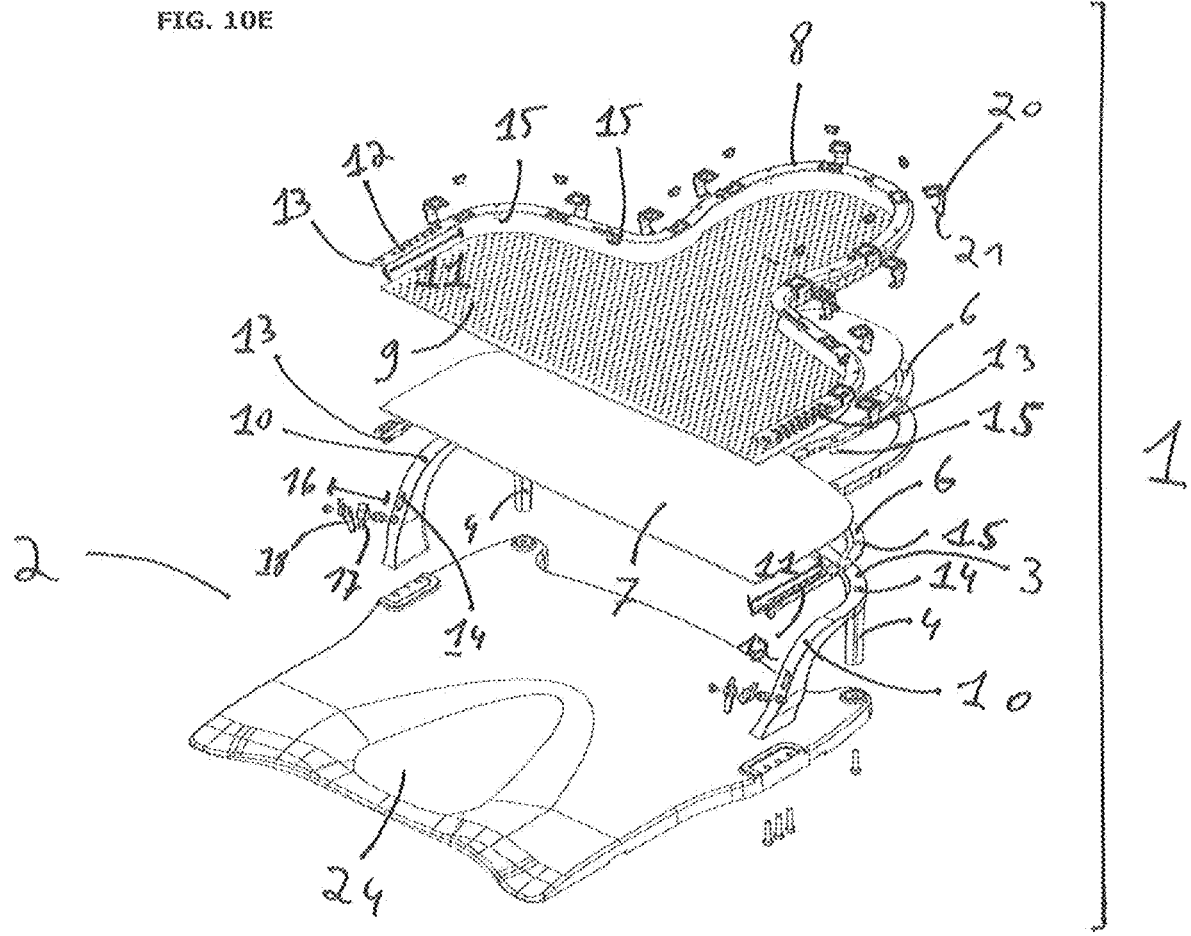
FIG. 10E shows an exploded three-dimensional representation of a system, using the device of FIG. 10A, for the immobilization of head, neck and shoulders, before use.
Figure 10F:
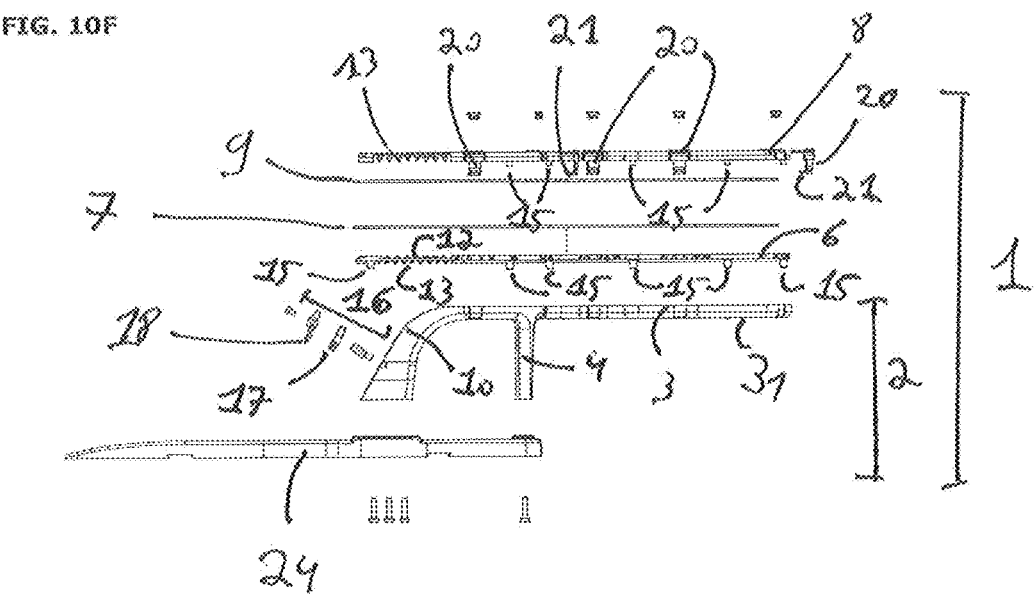
FIG. 10F shows an exploded side view of the system of FIG. 10E.
Figure 10G:
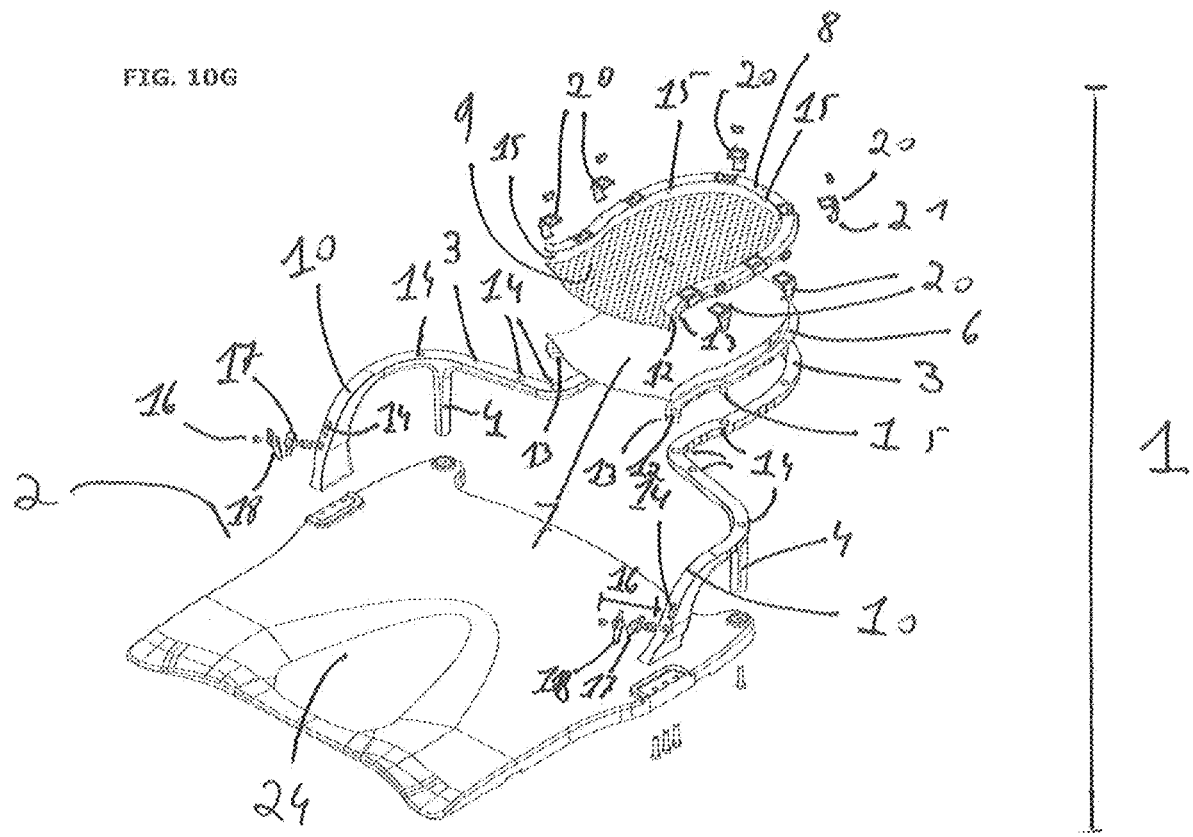
FIG. 10G shows an exploded three-dimensional representation of a system, using the device of FIG. 10A, for the immobilization of a head, before use.
Figure 10H:
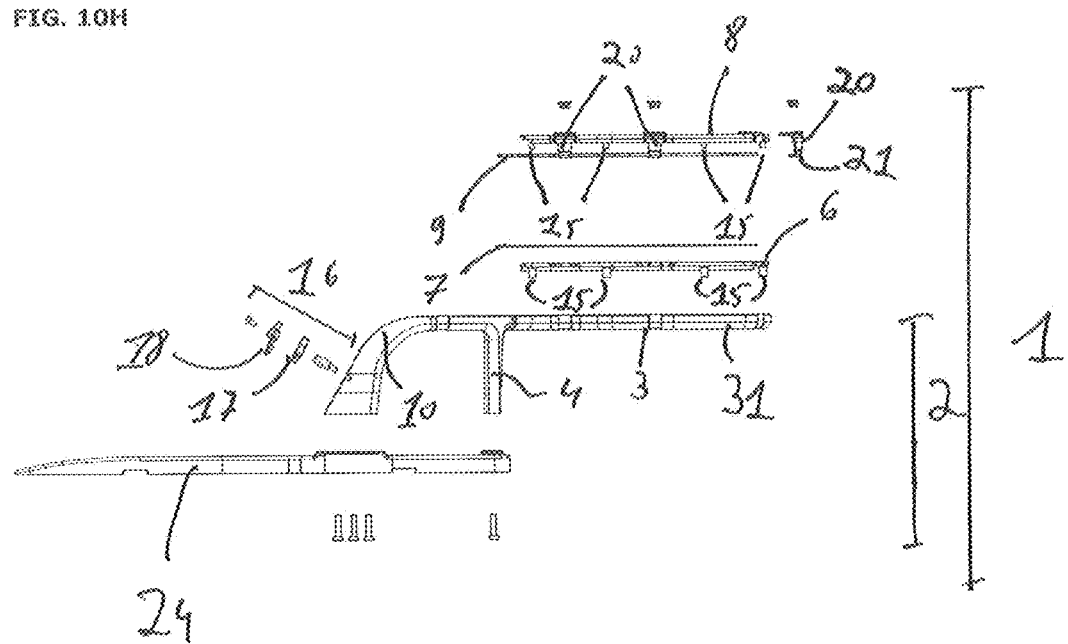
FIG. 10H shows an exploded side view of the system of FIG. 10G.

FIG. 10A shows a three-dimensional representation of even another alternative device according to an embodiment of the current invention. The device (2) has a very similar setup as the device of FIG. 6A. The base plate (24) is adapted for a fifth specific type of fixation surface (5). The base plate (24) comprise an embossment for receiving a patient's trunk. FIG. 10B shows a side view of the device of FIG. 10A. FIG. 10C shows a front view of the device of FIG. 10A. FIG. 10D shows a top view of the device of FIG. 10A. FIG. 10E shows an exploded three-dimensional representation of a system, using the device of FIG. 10A, for the immobilization of head and shoulders, before use. The system (1) comprises a device (2), as shown in FIGS. 10A-10D, a first frame (6) as shown in FIG. 5A and a second frame (8) as shown in FIG. 2A. Because the system (1) is shown before use, the first frame (6), the first sheet (7), the second frame (8) and the second sheet (9) are still flat. FIG. 10F shows an exploded side view of the system of FIG. 10E. FIG. 10G shows an exploded three-dimensional representation of a system, using the device of FIG. 10A, for the immobilization of a head, before use. The system (1) comprises a device (2), as shown in FIGS. 10A-10D, a first frame (6) as shown in FIG. 4 and a second frame (8) as shown in FIG. 3A. Because the system (1) is shown before use, the first frame (6), the first sheet (7), the second frame (8) and the second sheet (9) are still flat. FIG. 10H shows an exploded side view of the system of FIG. 10G.

Figure 11A:
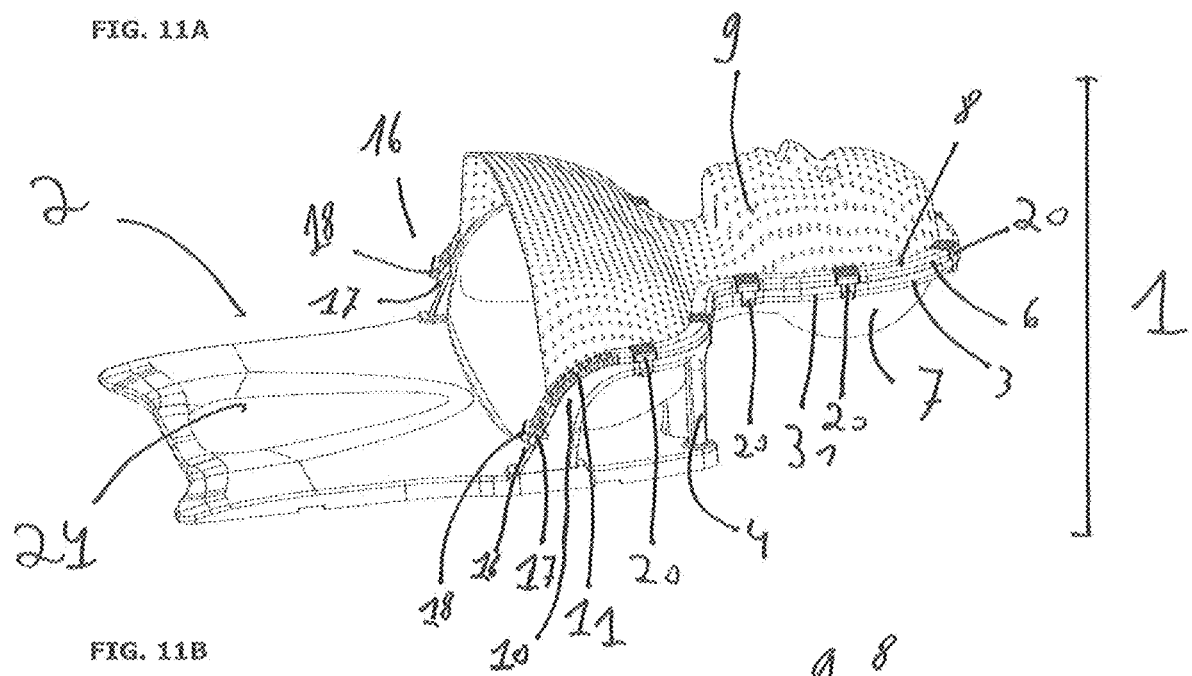
FIG. 11A shows a three-dimensional representation of a system, using the device of FIG. 10A, for the immobilization of head, neck and shoulders, during use.
Figure 11B:
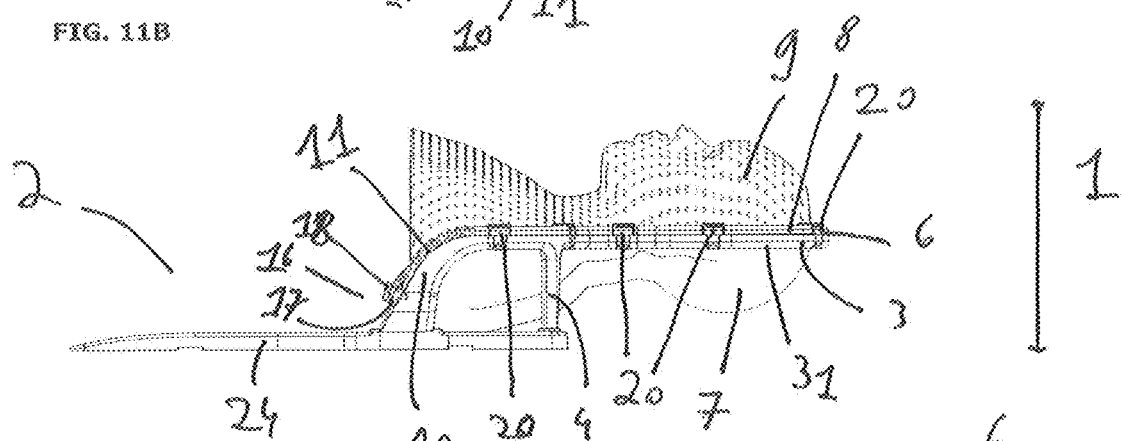
FIG. 11B shows a side view of the system of FIG. 11A.
Figure 11C:
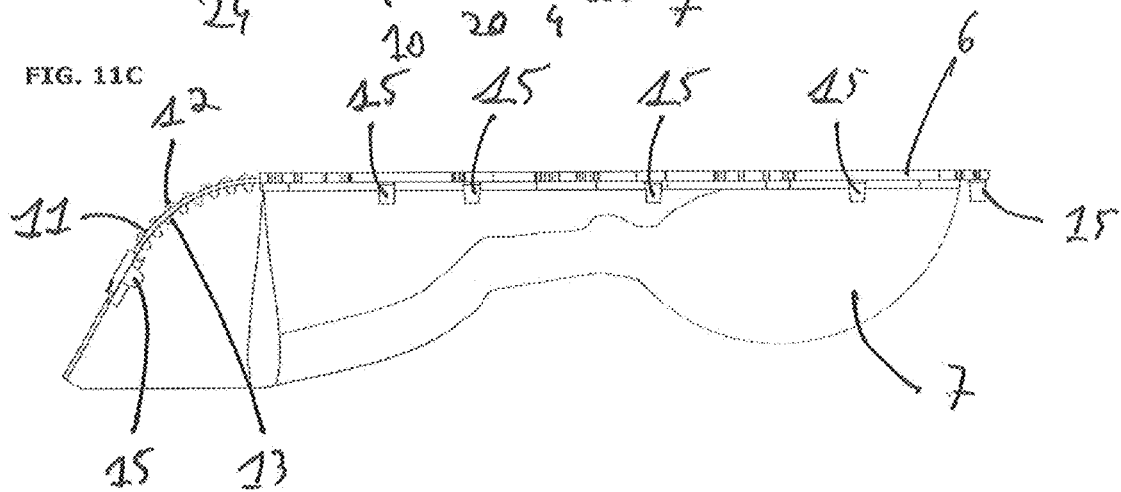
FIG. 11C shows a side view of the first frame of the system of FIG. 11A.
Figure 11D:
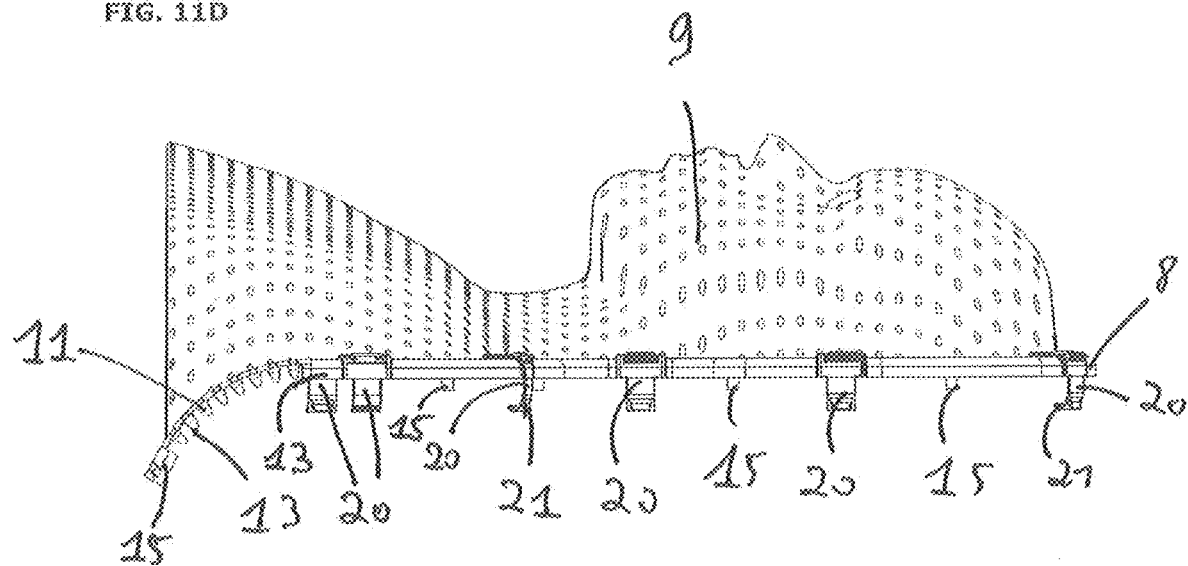
FIG. 11D shows a side view of the second frame of the system of FIG. 11A.
Figure 11E:
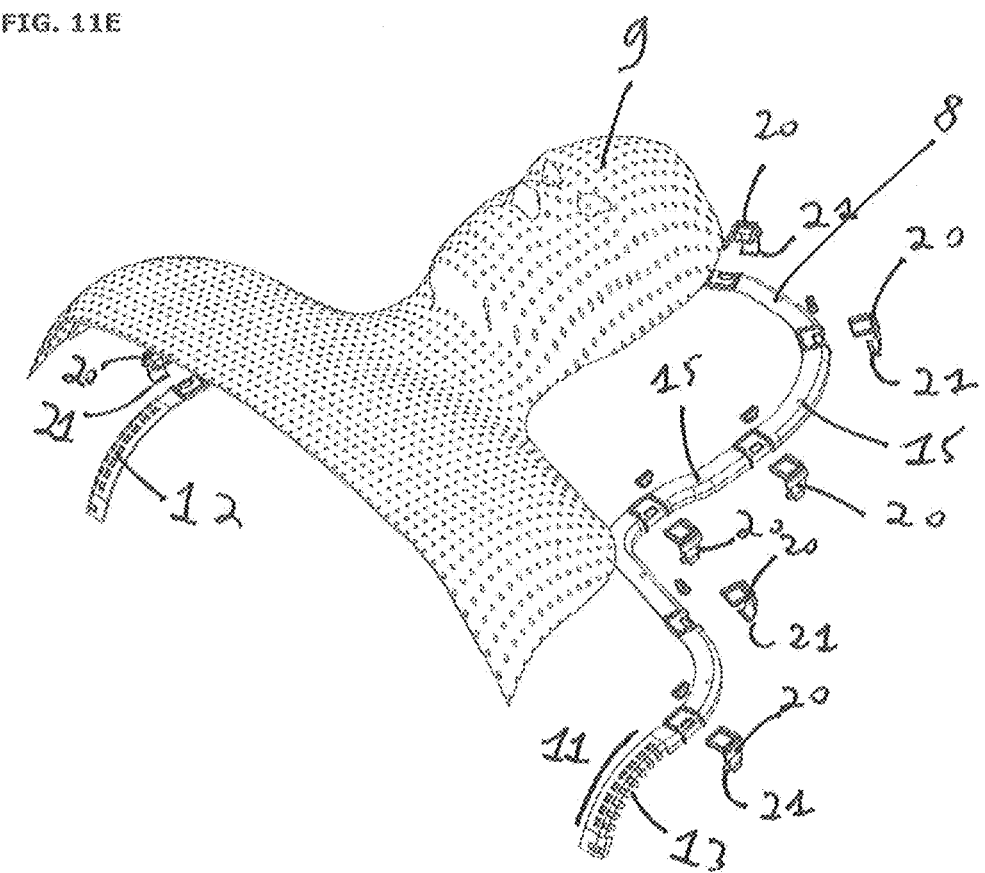
FIG. 11E shows an exploded three-dimensional representation of the second frame of the system of FIG. 11A.
Figure 11F:
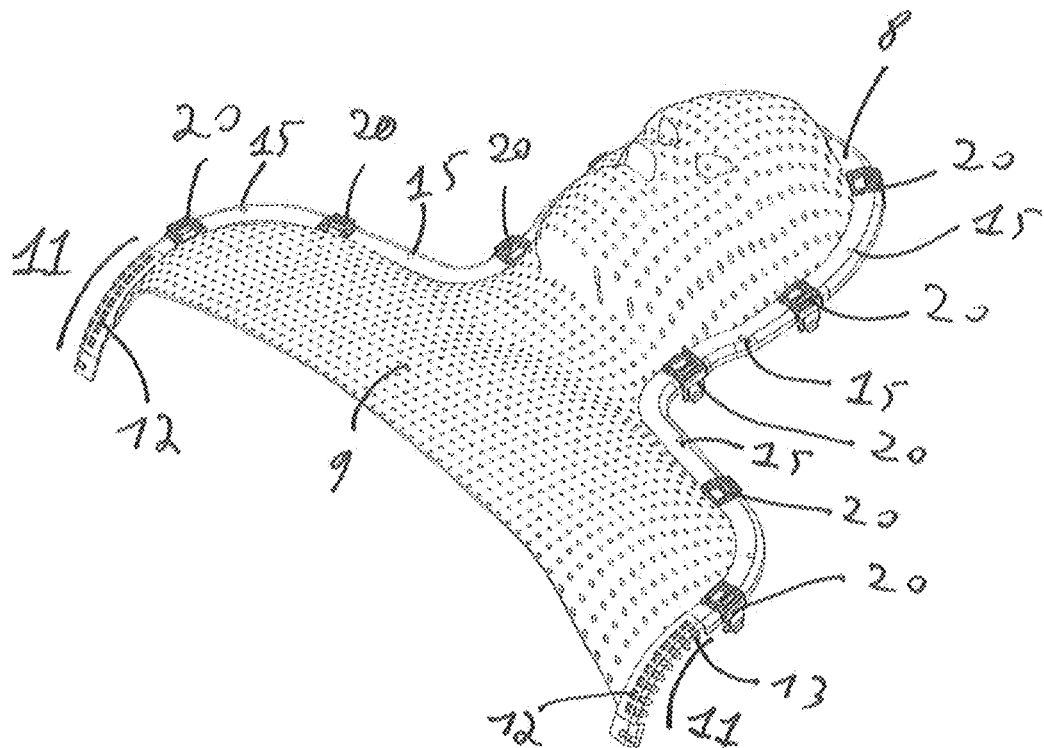
FIG. 11F shows a three-dimensional representation of the second frame of the system of FIG. 11A.

FIG. 11A shows a three-dimensional representation of a system, using the device of FIG. 10A, for the immobilization of head and shoulders, during use. The first frame (6) and the second frame (8) are bent to follow the curved extension (10) of the flanged support member (3). The first sheet (7) is molded and formed for covering anatomical contours of head, neck and shoulders and the second sheet (9) is molded and formed for covering anatomical contours of the head, neck and shoulders which is not covered by the first sheet (7). The first sheet (7) and the second sheet (9) form a double shell mask enclosing the head, neck and shoulders, leading to an optimal immobilization of the head, neck and shoulders. The patient is comfortable as also the neck and shoulders are supported. FIG. 11B shows a side view of the system of FIG. 11A. FIG. 11C shows a side view of the first frame of the system of FIG. 11A. It is clearly visible how the neck and shoulders are supported by the first sheet (9) up to close to the patient's trunk. The first frame (6) and the first sheet (7) can be dismounted from the device (3) of the system (1) after a radiotherapy session and stored for future follow up radiotherapy sessions while maintaining its shape. FIG. 11D shows a side view of the second frame of the system of FIG. 11A. It is clearly visible because the second sheet (9) does not have to be deformed until it touches the fixation surface (5) or in this case the base plate (24), the second sheet (9) can follow the anatomical contours of a first part of neck and shoulders more closely, resulting in an optimized immobilization of neck and shoulders. The second frame (8) and the second sheet (9) can be dismounted from the device (3) of the system (1) after a radiotherapy session and stored for future follow up radiotherapy sessions while maintaining its shape. FIG. 11E shows an exploded three-dimensional representation of the second frame of the system of FIG. 11A. FIG. 11F shows a three-dimensional representation of the second frame of the system of FIG. 11A.

Figure 12A:
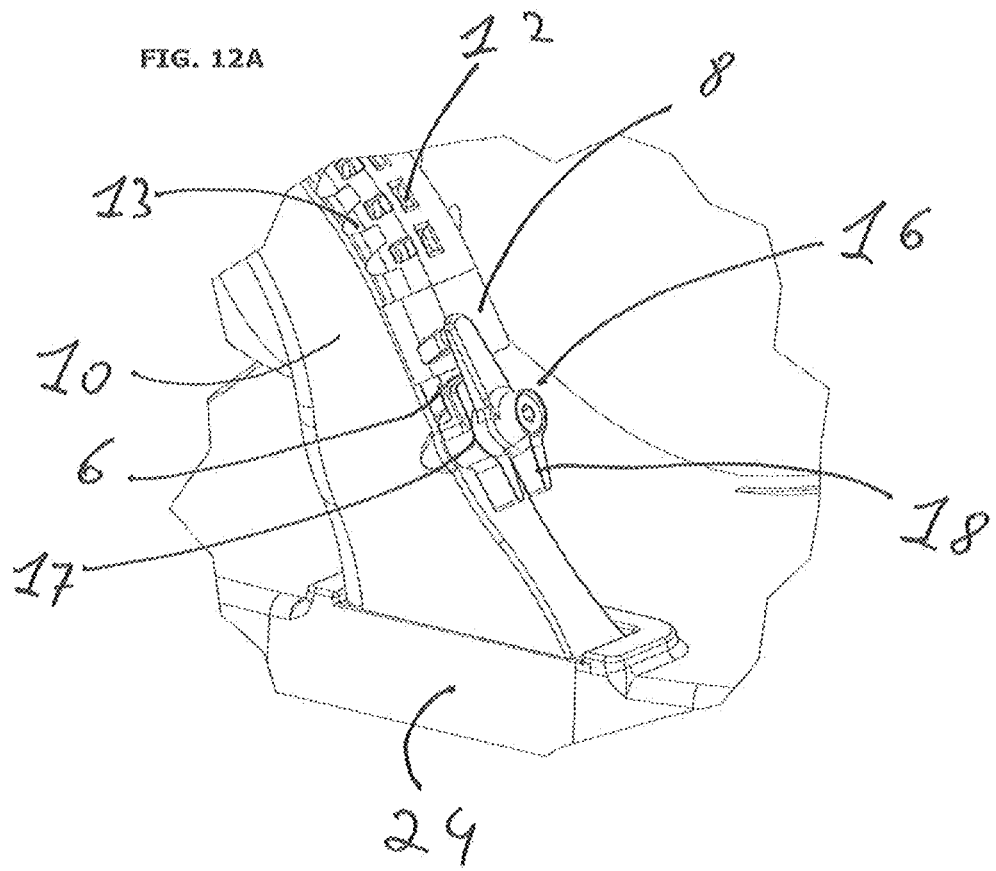
FIG. 12A shows a three-dimensional representation of a double locking mechanism according to an embodiment of the current invention.
Figure 12B:
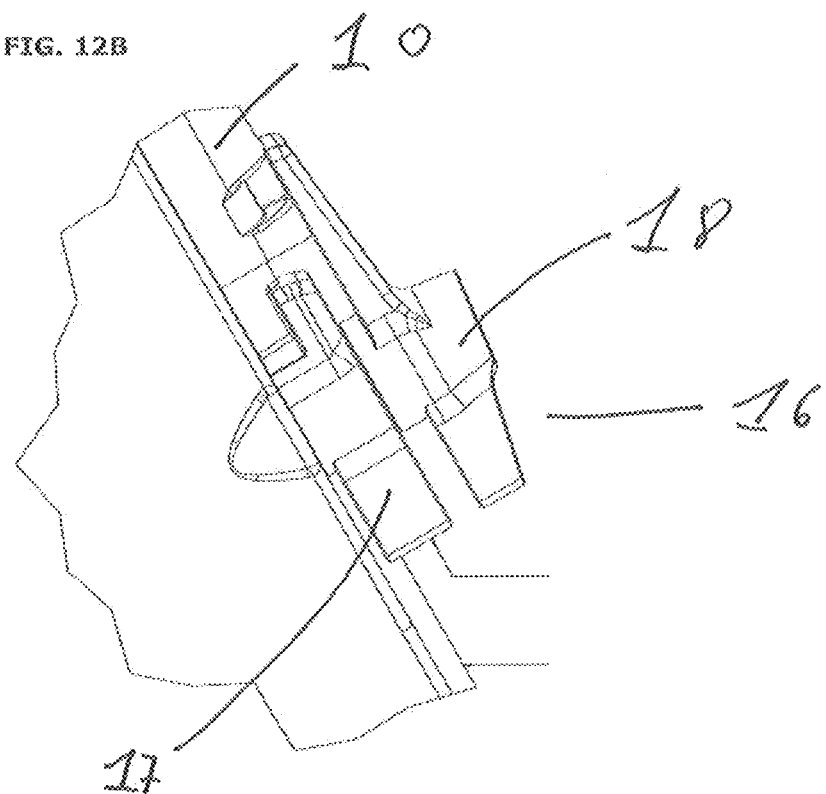
FIG. 12B shows a side view of the double locking mechanism of FIG. 12A.
Figure 12C:
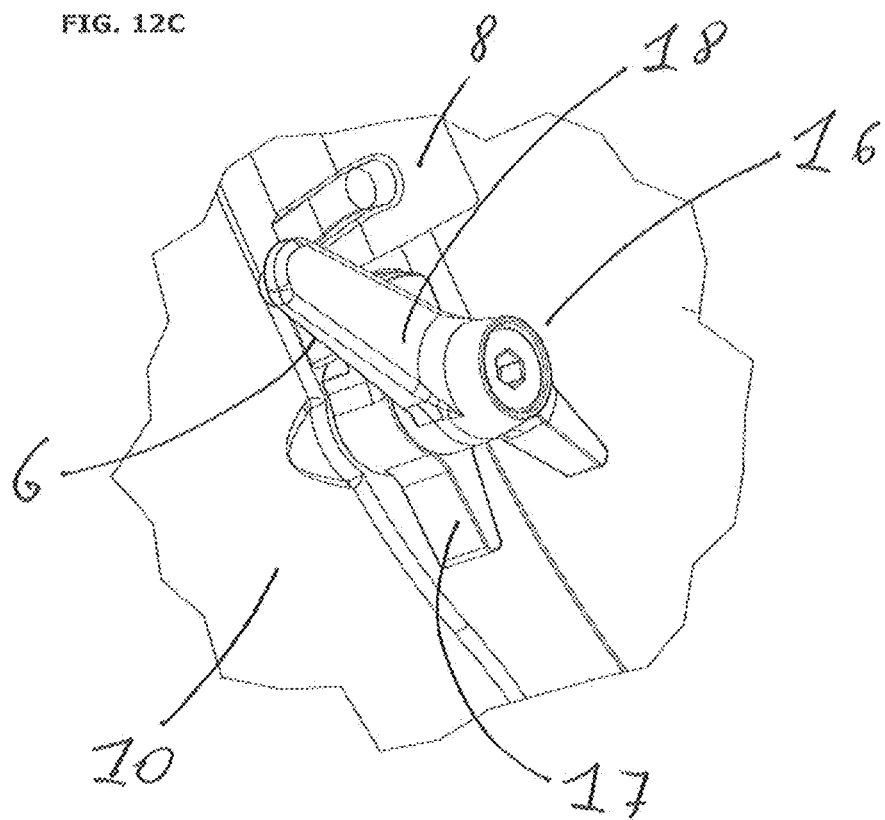
FIG. 12C shows a three-dimensional representation of the double locking mechanism of FIG. 12A, with the double locking mechanism in a locked position for a first frame and in an unlocked position for a second frame.
Figure 12D:
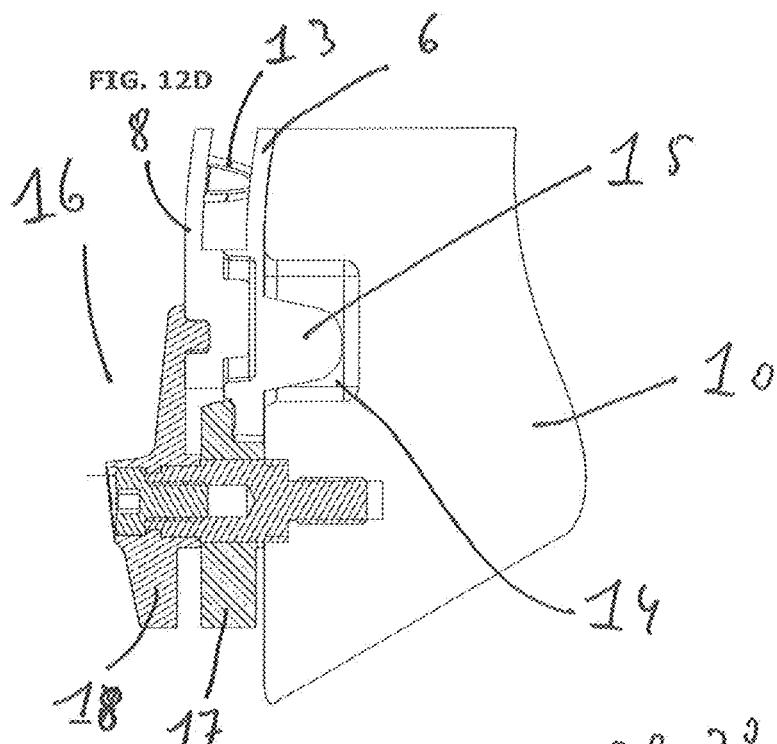
FIG. 12D shows a cross section of the double locking mechanism of FIG. 12A.
Figure 12E:
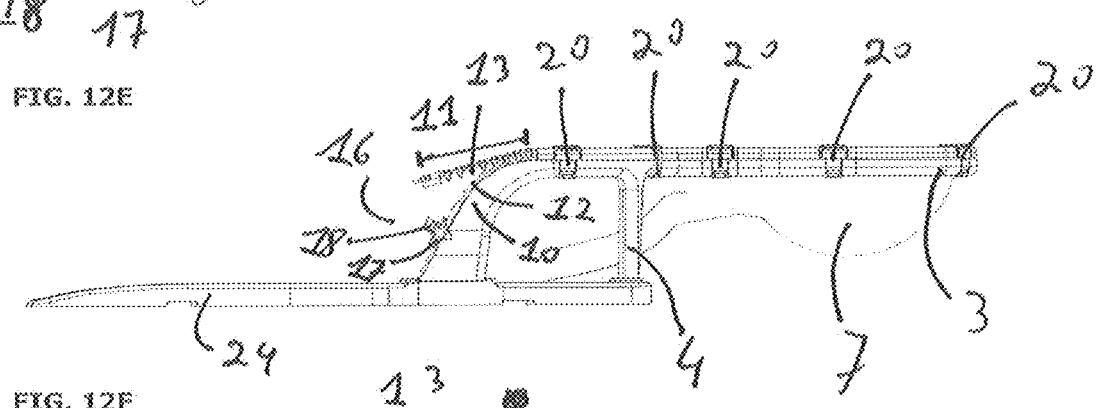
FIG. 12E shows side view of a system according to an embodiment of the current invention, with a first frame locked by the double locking mechanism of FIG. 12A and a second frame partially mounted.
Figure 12F:
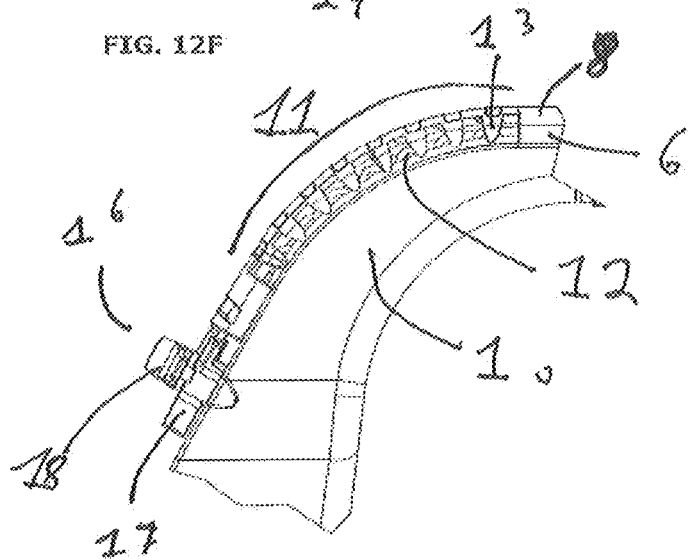
FIG. 12F shows side view of the system of FIG. 12E, with the first frame locked by the double locking mechanism and the second frame mounted, but not locked by the double locking mechanism.

FIG. 12A shows a three-dimensional representation of a double locking mechanism according to an embodiment of the current invention. The double locking mechanism (16) comprises a first rotatable lever (17) and a second rotatable lever (18). The first rotatable lever (17) and the second rotatable lever (18) are stacked on each other. The double locking mechanism (16) is placed on the curved extension (10). The first rotatable lever (17) is placed directly onto the curved extension (10) and the second rotatable lever (18) on the first rotatable lever (17). In a first position of the first rotatable lever (17), the first frame (6) is unlocked from the device (2). In a second position of the first rotatable lever (17), the first frame (6) is locked to the device (2). The first rotatable lever (17) is in the second position in FIG. 12A. In a first position of the second rotatable lever (18), the second frame (8) is unlocked from the device (2). In a second position of the second rotatable lever (18), the second frame (8) is locked to the device (2). The second rotatable lever (17) is in the second position in FIG. 12A. The double locking mechanism is advantageous for quickly locking the first frame (6) or second frame (8) to the curved extension (10) of the support member (3), while at the same time deforming the thermoplastic first sheet (7), respectively the thermoplastic second sheet (8). FIG. 12B shows a side view of the double locking mechanism of FIG. 12A. FIG. 12C shows a three-dimensional representation of the double locking mechanism of FIG. 12A, with the double locking mechanism in a locked position for a first frame and in an unlocked position for a second frame. FIG. 12D shows a cross section of the double locking mechanism of FIG. 12A. FIG. 12E shows side view of a system according to an embodiment of the current invention, with a first frame locked by the double locking mechanism of FIG. 12A and a second frame partially mounted. FIG. 12F shows side view of the system of FIG. 12E, with the first frame locked by the double locking mechanism and the second frame mounted, but not locked by the double locking mechanism.

Figure 13A:
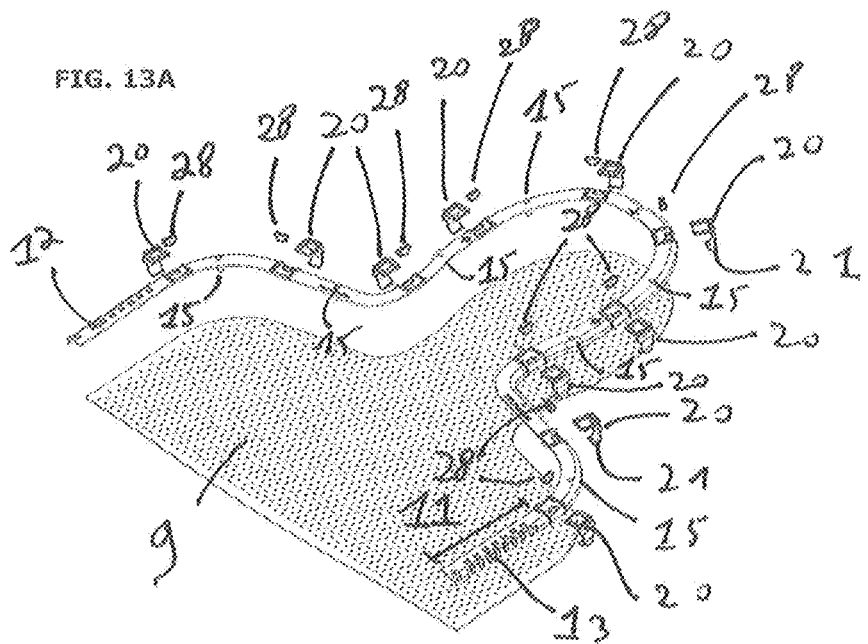
FIG. 13A shows an exploded three-dimensional representation of a second frame according to an embodiment of the current invention, for immobilization of head and shoulders, comprising clamps.
Figure 13B:
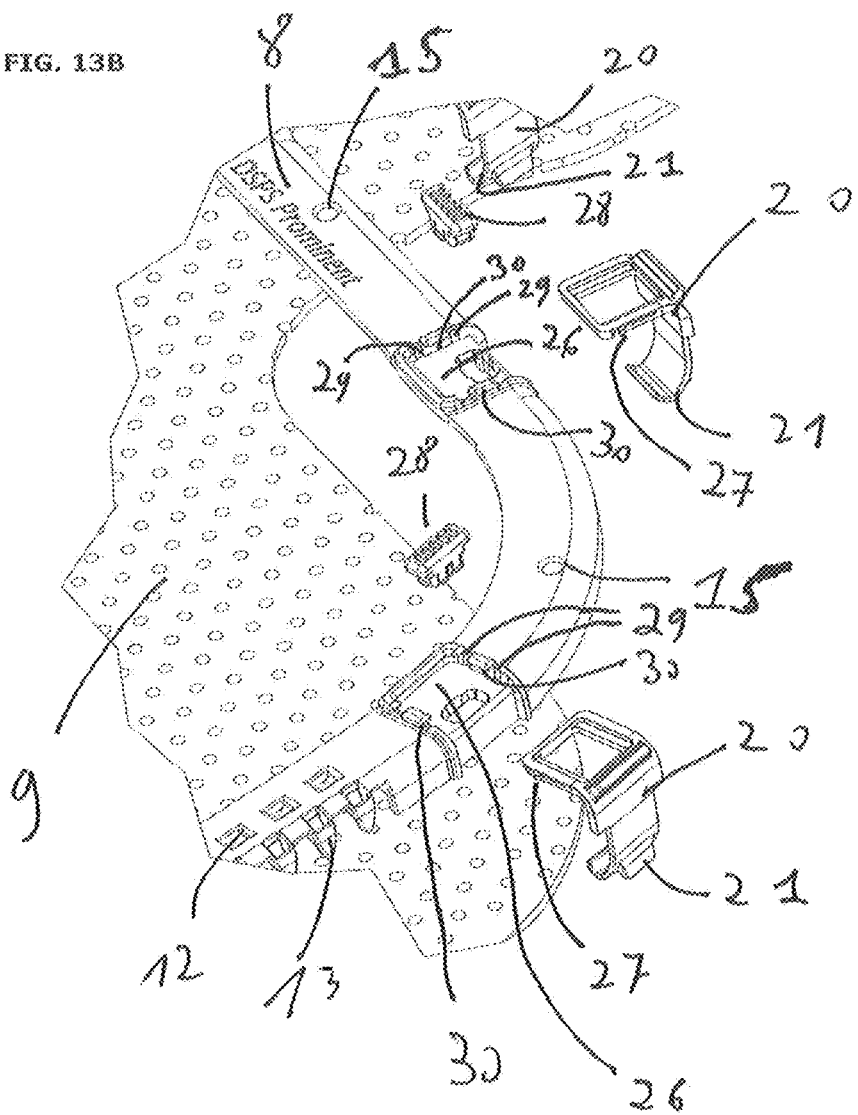
FIG. 13B shows a detail of FIG. 13A.
Figure 13F:
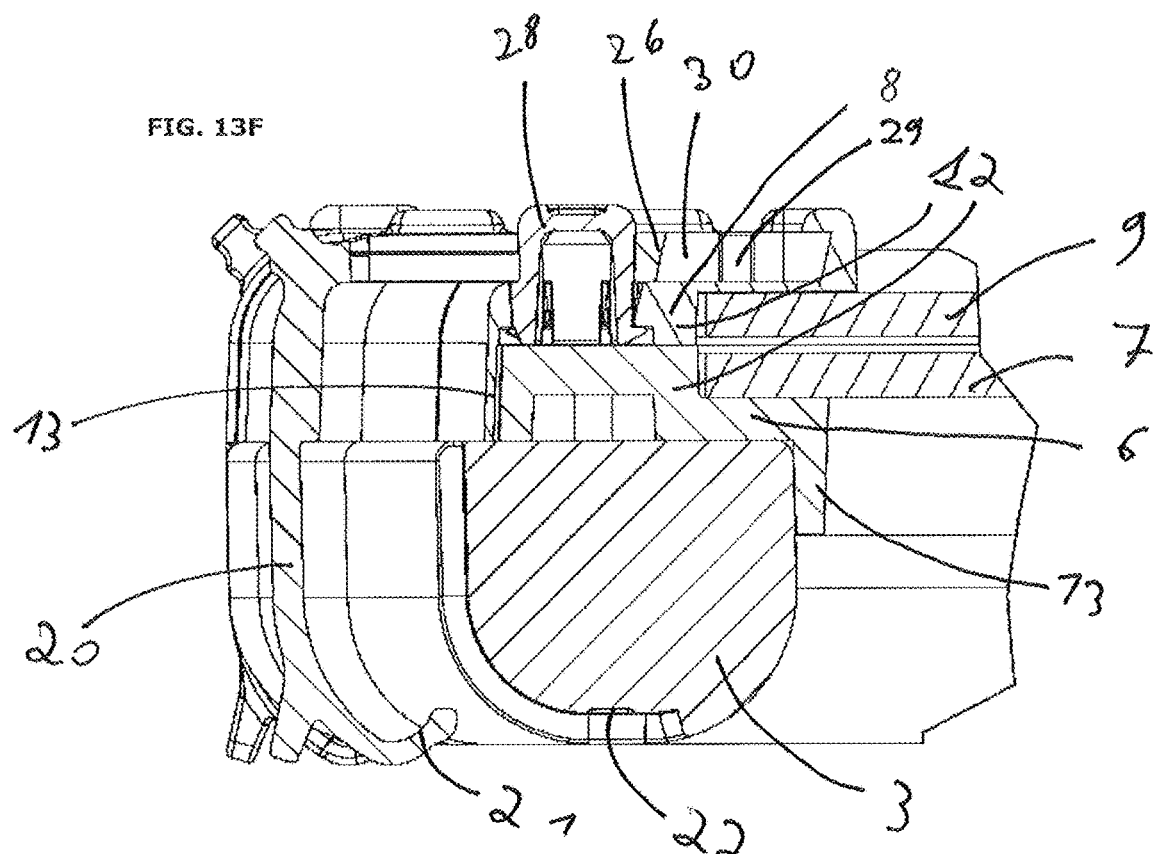
FIG. 13F shows a cross section of a clamp of FIG. 13A in a non-clamped position.
Figure 13G:
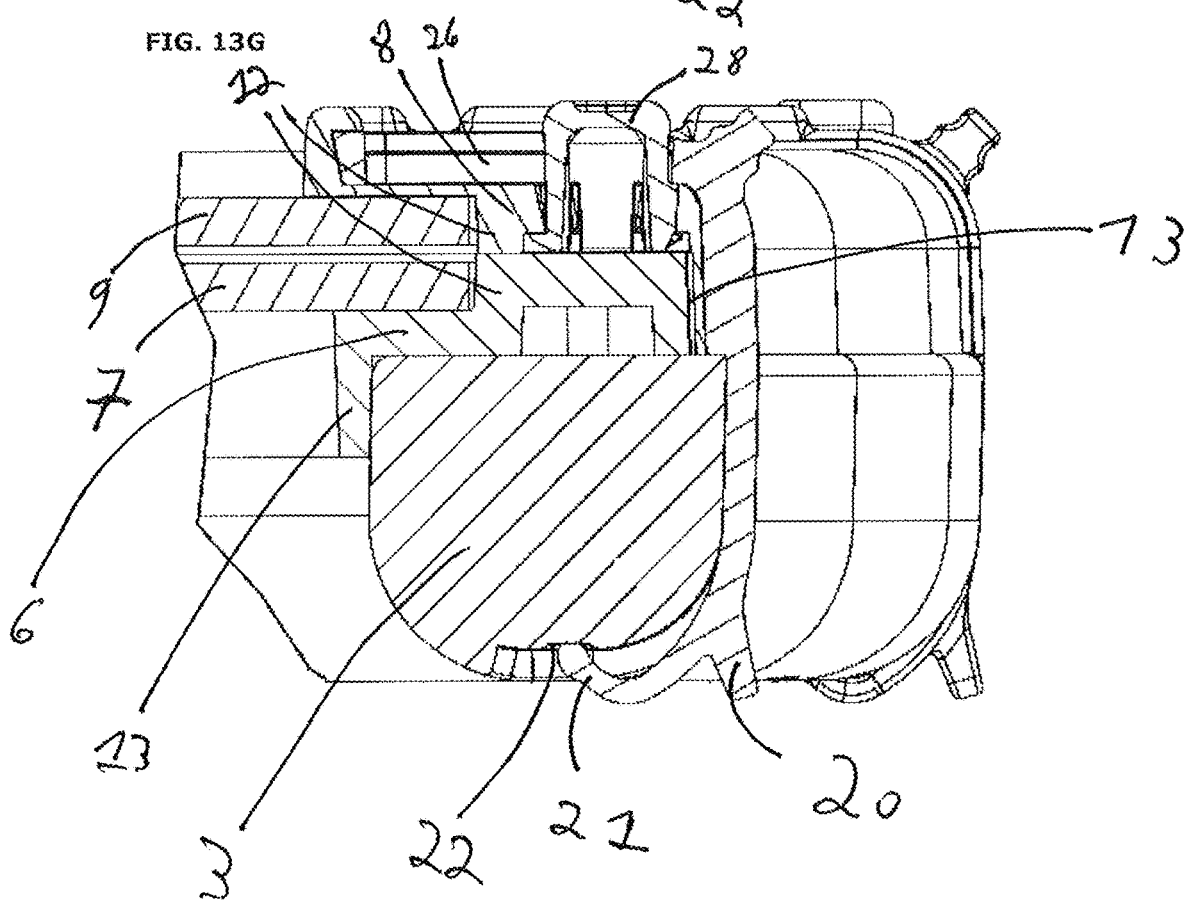
FIG. 13G shows a cross section of a clamp of FIG. 13A in a clamped position.

FIG. 13A shows an exploded three-dimensional representation of a second frame according to an embodiment of the current invention, for immobilization of head and shoulders, comprising clamps. The second frame (8) corresponds with the second frame of FIG. 2A. FIG. 13B shows a detail of FIG. 13A. The clamps (20) comprise a hook (21) to be removably attached to a flanged support member (3). The flanged support member (3) comprises a slot (26), allowing the clamp (20) to shift between a first position and a second position. In a first position the hook (21) is positioned beside the flanged support member (3). In a second position the hook (21) is attached to the flanged support member (3). The hook (21) is shiftable in a direction parallel to the plane formed by the second frame (8) and the second sheet (9). The slot (26) comprises guiding sides (30) for guiding the clamps (20) in the slot (26) from the first position to the second position and back. The clamps (20) comprise a flexible projection (27) for retaining the hook (21) in the first or second position. The slots (26) comprise complementary recesses (29) for receiving the projection. The clamps (20) comprise a retaining element (28) for obstructing removal of the clamps (20) from the slots (26). The retaining elements (28) comprise snap fit means for connecting the retaining elements (28) to the second frame (8). FIG. 13C shows a cross section of a clamp of FIG. 13A according to an embodiment of the current invention in a direction transverse to the clamp. FIG. 13D shows a cross section of a clamp of FIG. 13A at a first location in a direction parallel with the clamp. FIG. 13E shows a cross section of a clamp of FIG. 13A at a second location in a direction parallel with the clamp. FIG. 13F shows a cross section of a clamp of FIG. 13A in a non-clamped position. This is the first position of the clamp (20). FIG. 13G shows a cross section of a clamp of FIG. 13A in a clamped position. This is the second position of the clamp (20) The hook (21) is received in a notch (22) in the flanged support member (3).

Figure 14A:
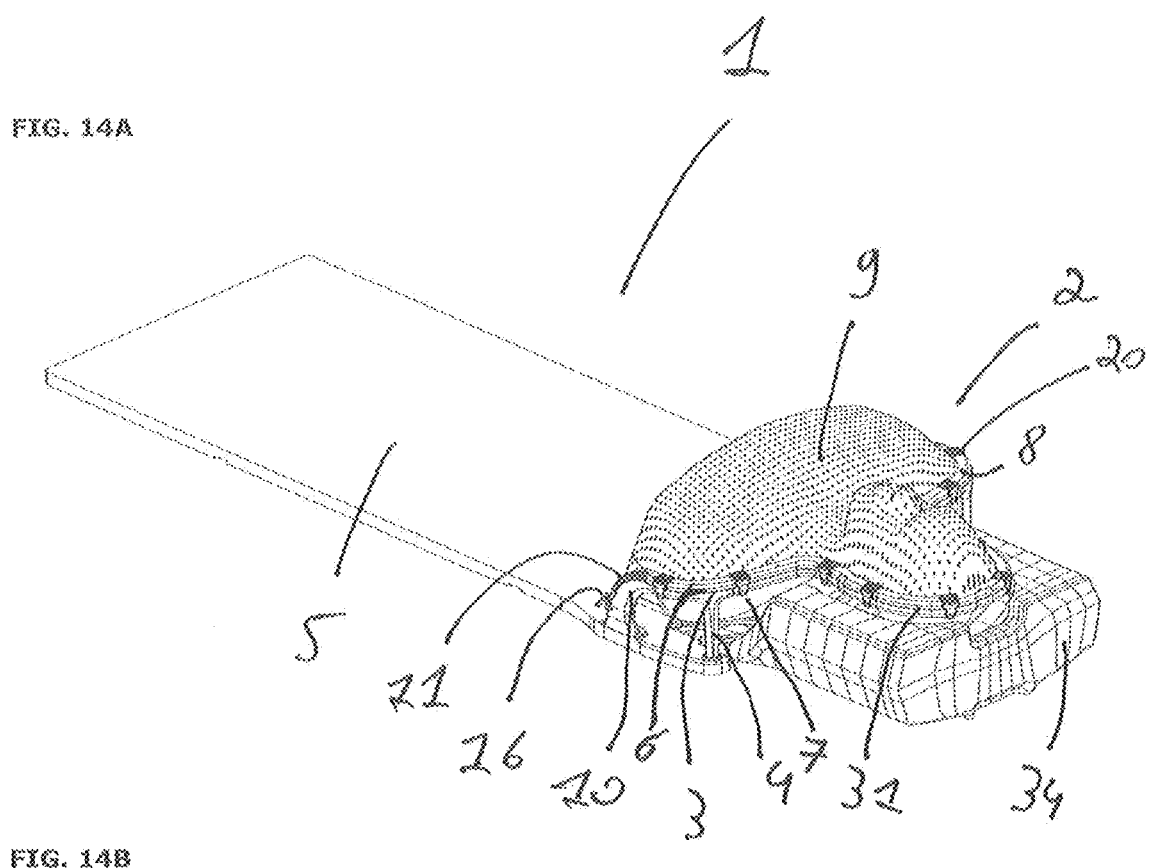
FIG. 14A shows a three-dimensional representation of a system according to an embodiment of the current invention in combination with a first half of a MRI head coil.
Figure 14B:
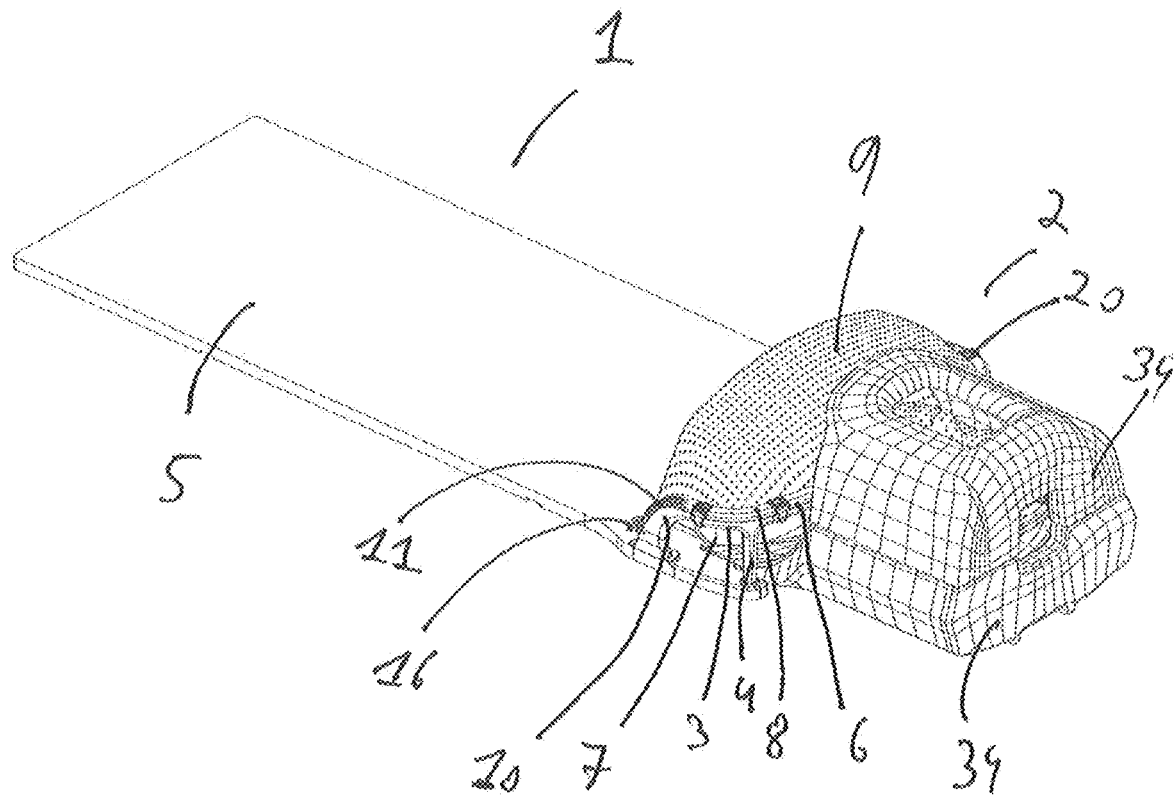
FIG. 14B shows a three-dimensional representation of the same system as in FIG. 14A with a completely closed MRI head coil.

FIG. 14A shows a three-dimensional representation of a system according to an embodiment of the current invention in combination with a first half of a head coil. The system (1) is similar to the previously described systems. The device (2) is attached to a fixation surface (5). The flanged support member (3) comprises a cantilevered part (31) at a side opposite to the curved extension (10). The cantilevered part (31) with the immobilized body part is entered in a head coil (34), for instance a MRI (Magnetic Resonance Imaging) head coil, not hindered by other structures like for instance the support member fixation means (4). On FIG. 14A, only a first bottom half of the head coil (34) is shown. FIG. 14B shows a three-dimensional representation of the same system as in FIG. 14A with a completely closed head coil.

Figure 15A:
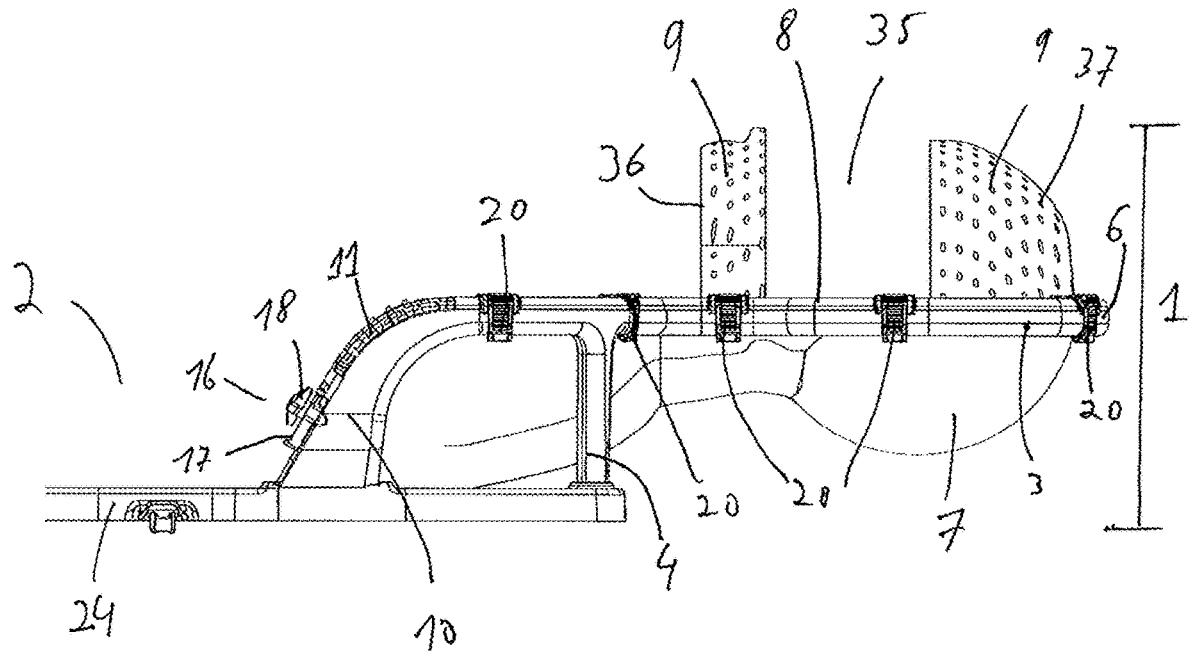
FIG. 15A shows a side view of a system according to an embodiment of the current invention, wherein the second sheet comprises a cutout.
Figure 15B:
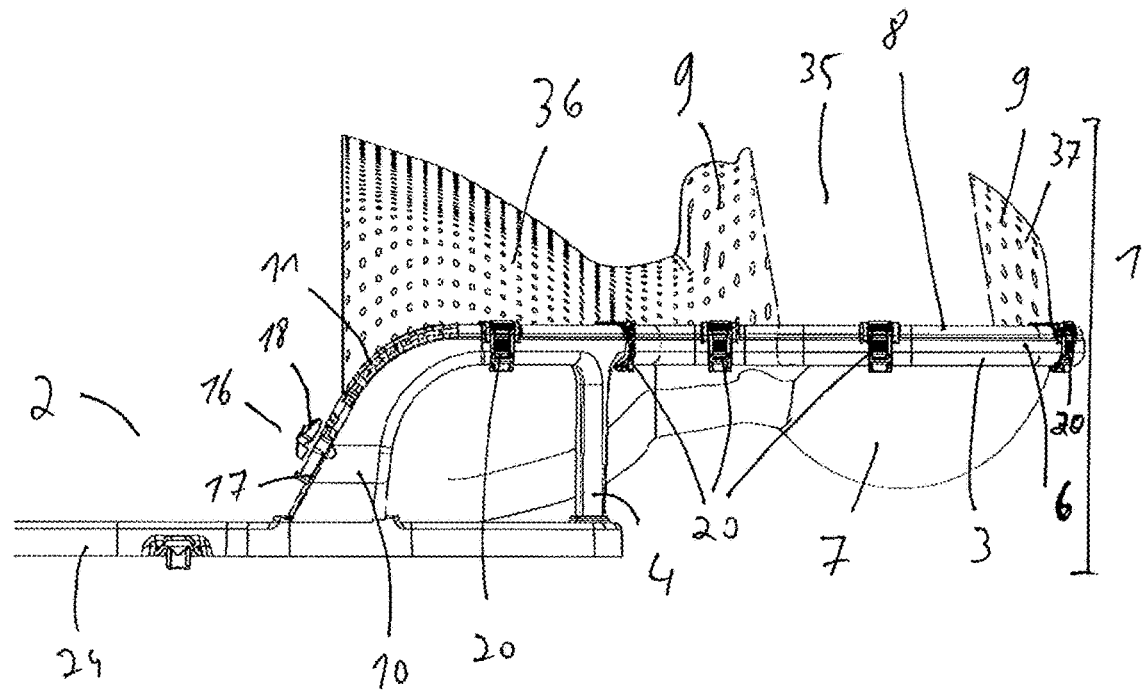
FIG. 15B shows a side view of a system according to an alternative embodiment of the current invention, wherein the second sheet comprises a cutout.

FIG. 15A shows a side view of a system according to an embodiment of the current invention, wherein the second sheet comprises a cutout. The second sheet (8) is similar to the second sheet (8) on FIG. 3A, with the exception of the cutout (35). The cutout (35) results in a first strap (36) and a second strap (37). The first strap (36) and the second strap (37) are extending from a first side of the second frame (8) to a second side of the second frame (8), opposite to the first side of the second frame (8). The patient body part is a head. The head is enclosed in a double shell mask formed by the first sheet (7), the first strap (36) and the second strap (37), strongly immobilizing the head. The first strap (36) is placed over the chin and the second strap (37) is placed over the forehead. The back of the head is completely and comfortably supported by the first sheet (7). The mouth and nose are free, reducing claustrophobic feelings and making breathing easier for a patient. The part of the head in between the first strap (36) and the second strap (37) remains visible. This is especially beneficial in case of SGRT. FIG. 15B shows a side view of a system according to an alternative embodiment of the current invention, wherein the second sheet comprises a cutout. The second sheet (8) is similar to the second sheet (8) on FIG. 2A, with the exception of the cutout (35). The first strap (36) is in this alternative embodiment placed over the chin and breast of the patient and the second strap (37) is placed over the top of the head.

The numbered references in the figures are:
1. System
2. Device
3. Flanged support member
4. Support member fixation means
5. Fixation surface
6. First frame
7. First sheet 8. Second frame
9. Second sheet
10. Curved extension
11. Deformable part
12. Positioning means
13. Guiding means
14. Openings
15. Protrusions
16. Double locking mechanism
17. First rotatable lever
18. Second rotatable lever
19. Attachment means
20. Clamp
21. Hook
22. Notch
23. Cutout for hair
24. Base plate
25. Fixation means
26. Slot
27. Projection
28. Retaining element
29. Recess
30. Guiding sides
31. Cantilevered part
32. Length of the cantilevered part
33. Total length of the flanged support member
34. Head coil
35. Cutout
36. First strap
37. Second strap It is supposed that the present invention is not restricted to any form of realization described previously and that some modifications can be added to the presented figures without reappraisal of the appended claims. For example, the present invention has been described referring to immobilization of head or head, neck and shoulders, but it is clear that the invention can be applied for immobilization of for instance legs or arms as well.

The invention claimed is:

1. A device for immobilization of a patient body part for radiotherapy applications comprising at least one flanged support member and at least one support member fixation means for mounting the at least one flanged support member to a fixation surface at a distance from said fixation surface, wherein the at least one flanged support member is adapted to receive and retain a first and optionally a second frame, characterized in that the at least one flanged support member comprises at one side a curved extension towards the fixation surface, wherein the curved extension is adapted to retain the first frame or the first frame and the second frame.

2. A system for immobilization of a patient body part for radiotherapy applications comprising:
a device comprising at least one flanged support member and at least one support member fixation means for mounting the at least one flanged support member to a fixation surface at a distance from said fixation surface, wherein the at least one flanged support member is adapted to receive and retain a first and a second frame;
a first frame, comprising a first sheet for covering anatomical contours of a first area of said body part, wherein the first frame forms a circumferential rim for the first sheet;
optionally a second frame, comprising a second sheet for covering anatomical contours of a second area of said body part which is not covered by the first sheet, wherein the second frame forms a circumferential rim for the second sheet, wherein the second frame is superimposable on the first frame, wherein the first sheet and the second sheet form a double shell mask enclosing said body part;
characterized in that the at least one flanged support member comprises at one side a curved extension towards the fixation surface, wherein the first frame or the first frame and the second frame are bent to follow the curved extension of the at least one flanged support member.

3. The system according to claim 2, wherein the first frame or the first frame and the second frame comprise at least at one side a deformable part, wherein the deformable part is deformable in a direction transverse to the fixation surface.

4. The system according to claim 3, wherein the first frame and the second frame comprise at an inner side, directed towards said sheets, positioning means for positioning said sheets in said frames and wherein on the deformable part of said frames the positioning means are open and separated protrusions.

5. The system according to claim 3, wherein the first frame and the second frame comprise guiding means for guiding the second frame to a correct position on the first frame and for guiding the first frame to a correct position on the at least one flanged support member and wherein on the deformable part of said frames the guiding means are separated protrusions.

6. The system according to claim 2, wherein the at least one flanged support member comprises openings and the first frame and the second frame comprise corresponding protrusions, wherein the protrusions of the first frame are hollow and received in the openings of the at least one flanged support member and the curved extension and wherein the protrusions of the second frame are received in the hollow protrusions of the first frame.

7. The system according to claim 2, wherein the device comprises a double locking mechanism, comprising a first rotatable lever and a second rotatable lever, wherein the first rotatable lever and the second rotatable lever are stacked on each other, wherein the first frame is locked to the device with the first rotatable lever in a first position and unlocked to the device with the first rotatable lever in a second position and wherein the second frame is locked to the device with the second rotatable lever in a second position and unlocked to the device with the second rotatable lever in a second position.

8. The system according to claim 2, wherein the second frame comprises clamps for securing the first and the second frame to the at least one flanged support member, wherein the clamps are attached to a first side of the second frame and removably attached to the at least one flanged support member and wherein the first frame is positioned in between the at least one flanged support member and the second frame.

9. The system according to the claim 8, wherein the clamps comprise a hook and the at least one flanged support member a corresponding notch for receiving the hook.

10. The system according to claim 2, wherein the second sheet comprises a cutout, resulting in a first strap and a second strap, wherein the first strap and the second strap are extending from a first side of the second frame to a second side of the second frame, opposite to the first side.

11. A method for immobilization of a patient body part for radiotherapy applications comprising the steps of:
mounting a device comprising at least one flanged support member and at least one support member fixation means to a fixation surface, wherein the at least one flanged support member is mounted with the at least one support member fixation means to the fixation surface at a distance from said fixation surface, wherein the at least one flanged support member is adapted to receive and retain a first and optionally a second frame;

mounting a first frame, comprising a first sheet, to the at least one flanged support member;

placing the patient body part to be immobilized on the first sheet thereby covering the anatomical contours of a first area of said body part;

optionally mounting a second frame, comprising a second sheet, on the first frame to the at least one flanged support member thereby covering the anatomical contours of a second area of said body part which is not covered by the first sheet, to form a double shell mask enclosing said body part;

characterized in that, the at least one flanged support member comprises at one side a curved extension towards the fixation surface, wherein the first frame or the first frame and the second frame are bent to follow the curved extension of the at least one flanged support member.

12. The method according to claim 11, wherein the first frame or the first frame and the second frame are flat before initial use and comprise at least at one side a deformable part, wherein the deformable part is being deformed in a direction transverse to the fixation surface to follow the curved extension of the at least one flanged support member.

13. The method according to claim 11, wherein the first frame and the second frame are secured to the at least one flanged support member by removably attaching clamps to the at least one flanged support member, wherein the clamps are attached to a first side of the second frame and wherein the first frame is positioned in between the at least one flanged support member and the second frame.

14. The method according to claim 11, wherein the first frame is locked to the device by rotating a first rotatable lever of a double locking mechanism from a first position to a second position, wherein the second frame is locked to the device by rotating a second rotatable lever of the double locking mechanism from a first position to a second position and wherein the first rotatable lever and the second rotatable lever are stacked on each other.

15. The method according to claim 11, wherein the second sheet comprises a cutout, resulting in a first strap and a second strap, wherein the first strap and the second strap are extending from a first side of the second frame to a second side of the second frame, opposite to the first side and wherein the first strap and the second strap immobilize the patient body part, leaving the patient body part visible in between the first strap and the second strap.

16. A kit for immobilization of a patient body part for radiotherapy applications, comprising:
  a device, comprising at least one flanged support member and at least one support member fixation means for mounting the at least one flanged support member to a fixation surface at a distance from said fixation surface;
  a first frame, comprising a first sheet, wherein the first frame forms a circumferential rim for the first sheet;
  optionally a second frame, comprising a second sheet, wherein the second frame forms a circumferential rim for the second sheet, wherein the second frame is superimposable on the first frame;
  characterized in that the at least one flanged support member comprises at one side a curved extension towards the fixation surface, wherein the first frame or the first frame and the second frame are flat and comprise at least at one side a deformable part, wherein the deformable part is deformable in a direction transverse to the fixation surface.

17. The kit according to claim 16, wherein the kit further comprises clamps for securing the first frame and the second frame to the at least one flanged support member.

18. The kit according to claim 16, wherein the second sheet comprises a cutout, resulting in a first strap and a second strap, wherein the first strap and the second strap are extending from a first side of the second frame to a second side of the second frame, opposite to the first side.

* * * * *